(12) United States Patent
Wagner et al.

(10) Patent No.: US 6,576,478 B1
(45) Date of Patent: *Jun. 10, 2003

(54) MICRODEVICES FOR HIGH-THROUGHPUT SCREENING OF BIOMOLECULES

(75) Inventors: Peter Wagner, Cupertino, CA (US); Dana Ault-Riche, Palo Alto, CA (US); Steffen Nock, Palo Alto, CA (US); Christian Itin, Menlo Park, CA (US)

(73) Assignee: Zyomyx, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/115,397

(22) Filed: Jul. 14, 1998

(51) Int. Cl.$^7$ ............................................. G01N 33/543
(52) U.S. Cl. ........................ 436/518; 427/261; 427/287; 427/387; 427/407.2; 435/4; 435/7.1; 435/288.2; 435/288.5; 435/287.1; 435/6; 436/514
(58) Field of Search ............................... 548/303.7, 303, 548/303.1; 427/261, 287, 387, 407.2; 435/4, 7.1, 131, 288.2, 288.5, 287.1, 6; 436/514, 518

(56) References Cited

U.S. PATENT DOCUMENTS

| | | | |
|---|---|---|---|
| 4,071,409 A | 1/1978 | Messing et al. | |
| 4,562,157 A | 12/1985 | Lowe et al. | 435/291 |
| 4,690,715 A | 9/1987 | Allara et al. | 148/6.15 |
| 4,722,896 A | 2/1988 | Kadish et al. | |
| 4,908,112 A | 3/1990 | Pace | 204/299 |
| 4,973,493 A | 11/1990 | Guire | 427/2 |

(List continued on next page.)

FOREIGN PATENT DOCUMENTS

| | | |
|---|---|---|
| DE | 3939973 A1 | 6/1991 |
| DE | 19543232 A1 | 5/1997 |
| EP | 596421 A1 | 5/1994 |
| EP | 780423 A2 | 6/1997 |
| JP | 60-41183 | 2/1994 |
| JP | 70-84372 | 3/1995 |

(List continued on next page.)

OTHER PUBLICATIONS

Cha et al. Expression of fused protein, human interleukin–2 and green fluorescent protein, in insect larvae. Annual Meeting of The American Institute of Chemical Engineers, Los Angeles, CA, Nov. 1997.*

Kemeny. Enzyme–linked immunoassay. In Immuno–Chemistry 1 (Eds Johnstone and Turner). pp. 147–175, Nov. 1997.*

Mauracher et al. Reduction of rubella ELISA background using denatured sample buffer. J. Immunol. Methods. 145:251–254, 1991.*

Jacobson et al. Fused quartz substrates for microchip electorphoresis. Anal Chem. 67:2059–2063, Aug. 1, 1995.*

Martynova et al. Fabrication of plastic microfluid channels by imprinting methods. Anal. Chem. 69:4783–4789, Dec. 1, 1997.*

Elkins et al. (1991). Multianalyte microspot immunoassay–microanalytical "compact disk" of the future. Clin. Chem. 37(11):1955–1967.*

Kricka (1998). Miniaturization of analytical systems. Clin. Chem. 44(9):2008–2014.*

(List continued on next page.)

*Primary Examiner*—Christopher L. Chin
(74) *Attorney, Agent, or Firm*—Townsend, Townsend and Crew

(57) ABSTRACT

Devices for the parallel, in vitro screening of biomolecular activity using miniaturized microfabricated devices are provided. The biomolecules that can be immobilized on the surface of the devices of the present invention include proteins, polypeptides, nucleic acids, polysaccharides, phospholipids, and related unnatural polymers of biological relevance. These devices are useful in high-throughput drug screening and clinical diagnostics and are preferably used for the parallel screening of families of related proteins.

10 Claims, 10 Drawing Sheets

Top view

U.S. PATENT DOCUMENTS

| | | |
|---|---|---|
| 4,987,032 A | 1/1991 | Miyasaka et al. |
| 5,079,600 A | 1/1992 | Schnur et al. ................. 357/4 |
| 5,096,807 A | 3/1992 | Leaback |
| 5,143,854 A | 9/1992 | Pirrung et al. .............. 436/518 |
| 5,154,808 A | 10/1992 | Miyasaka et al. |
| 5,160,597 A | 11/1992 | Colapicchiori et al. ..... 204/403 |
| 5,242,828 A | 9/1993 | Bergstrom et al. .......... 435/291 |
| 5,252,743 A * | 10/1993 | Barrett et al. ............ 548/303.7 |
| 5,294,369 A | 3/1994 | Shigekawa et al. ...... 252/313.1 |
| 5,296,114 A * | 3/1994 | Manz ......................... 204/180 |
| 5,296,144 A * | 3/1994 | Manz ......................... 204/180 |
| 5,304,487 A * | 4/1994 | Wilding et al. ............. 435/291 |
| 5,342,692 A | 8/1994 | Ribi ........................... 428/420 |
| 5,384,261 A | 1/1995 | Winkler et al. ............. 436/518 |
| 5,405,766 A | 4/1995 | Kallury et al. .............. 435/174 |
| 5,405,783 A | 4/1995 | Pirrung et al. .............. 436/518 |
| 5,412,087 A | 5/1995 | McGall et al. ............. 536/24.3 |
| 5,429,708 A | 7/1995 | Linford et al. ................ 216/66 |
| 5,441,876 A * | 8/1995 | Singh ......................... 435/131 |
| 5,445,934 A | 8/1995 | Fodor et al. .................... 435/6 |
| 5,472,881 A | 12/1995 | Beebe et al. ................. 436/94 |
| 5,510,270 A | 4/1996 | Fodor et al. ................ 436/518 |
| 5,512,131 A | 4/1996 | Kumar et al ............. 156/655.1 |
| 5,512,492 A | 4/1996 | Herron et al. .............. 436/518 |
| 5,514,501 A | 5/1996 | Tarlov ........................... 430/5 |
| 5,520,787 A | 5/1996 | Hanagan et al. ............ 204/409 |
| 5,571,410 A | 11/1996 | Swedberg et al. ....... 210/198.2 |
| 5,593,838 A | 1/1997 | Zanzucchi et al. ............. 435/6 |
| 5,603,351 A | 2/1997 | Cherukuri et al. .......... 137/597 |
| 5,605,662 A | 2/1997 | Heller et al. ............... 422/68.1 |
| 5,620,850 A * | 4/1997 | Bamdad et al. ............. 530/300 |
| 5,622,826 A | 4/1997 | Varma .......................... 435/6 |
| 5,624,711 A * | 4/1997 | Sundberg et al. ........... 427/261 |
| 5,629,213 A | 5/1997 | Kornguth et al. ........... 436/518 |
| 5,635,358 A | 6/1997 | Wilding et al. ............. 435/7.2 |
| 5,637,469 A * | 6/1997 | Wilding et al. ............ 435/7.21 |
| 5,677,195 A | 10/1997 | Winkler et al. ............. 436/518 |
| 5,677,196 A | 10/1997 | Herron et al. .............. 436/518 |
| 5,681,484 A * | 10/1997 | Zanzucchi et al. ............. 216/2 |
| 5,688,642 A | 11/1997 | Chrisey et al. ................ 435/6 |
| 5,700,642 A | 12/1997 | Monforte et al. .............. 435/6 |
| 5,719,060 A | 2/1998 | Hutchens et al. ........... 436/174 |
| 5,726,026 A * | 3/1998 | Wilding et al. ............ 436/7.21 |
| 5,731,152 A | 3/1998 | Maracas et al. .................. 3/98 |
| 5,744,305 A | 4/1998 | Fodor et al. .................... 435/6 |
| 5,766,908 A * | 6/1998 | Klein et al. ................. 435/179 |
| 5,776,674 A | 7/1998 | Ulmer |
| 5,837,832 A | 11/1998 | Chee et al. |
| 5,843,767 A | 12/1998 | Beattie et al. |
| 5,849,208 A | 12/1998 | Hayes et al. |
| 5,858,188 A * | 1/1999 | Soane et al. ................ 204/454 |
| 5,861,242 A | 1/1999 | Chee et al. |
| 5,866,345 A | 2/1999 | Wilding et al. |
| 5,919,523 A | 7/1999 | Sundberg et al. |
| 5,925,552 A | 7/1999 | Keogh et al. |
| 5,928,880 A | 7/1999 | Wilding et al. |
| 5,942,443 A * | 8/1999 | Parce et al. ................. 436/514 |
| 6,046,056 A | 4/2000 | Parce et al. |
| 6,048,709 A | 4/2000 | Falb |

FOREIGN PATENT DOCUMENTS

| | | |
|---|---|---|
| WO | WO 91/16425 | 10/1991 |
| WO | WO 93/21528 | 10/1993 |
| WO | WO9850773 | 11/1994 |
| WO | WO 95/08770 | 3/1995 |
| WO | WO9535505 | 12/1995 |
| WO | WO 96/02830 | 2/1996 |
| WO | WO 96/10178 | 4/1996 |
| WO | WO 96/26432 | 8/1996 |
| WO | WO 96/29629 | 9/1996 |
| WO | WO 96/38726 | 12/1996 |
| WO | WO 96/39937 | 12/1996 |
| WO | WO 97/07429 | 2/1997 |
| WO | WO 97/21094 | 6/1997 |
| WO | WO 97/33737 | 9/1997 |
| WO | WO 97/36681 | 10/1997 |
| WO | WO 97/41424 | 11/1997 |
| WO | WO 97/41425 | 11/1997 |
| WO | WO9823948 | 6/1998 |
| WO | WO9839481 | 9/1998 |
| WO | WO 99/40434 | 8/1999 |
| WO | WO 00/52209 | 9/2000 |
| WO | WO 00/53625 | 9/2000 |
| WO | WO 00/54046 | 9/2000 |

OTHER PUBLICATIONS

Ekins (1998). Ligand assays; from electryophoresis to miniaturized microarrays. Clin. Chem. 44(9):2015–2030.*

Silzel et al. (1998). Mass–sensing, multianalyte microarray immunoassay with imaging detection. Clin. Chem. 44(9):2036–2043.*

Rowe et al. (1999) Array biosensor for simultaneous identification of bacterial, viral protein analytes. Anal. Chem. 71(17):3846–3852.*

Dzgoev et al. (1996). Microformat imaging ELISA for pesticide determination. Anal. Chem. 68(19):3364–3369.*

Jones et al. (1998). Microminiaturized immunoassays using atomic force microscopy and compositionally patterned antigen arrays. Anal. Chem. 70(7):1223–1241.*

Martynova et al. (1997). Fabricating of plastic microfluid channels by imprinting methods. Anal. Chem. 69:4783–4789.*

Becker et al., "Fabrication of microstructures with high aspect ratios and great structural heights by synchrotron radiation lithography, glavanoforming, and plastic moulding (LIGA process)," *Microelectronic Engineering,* 4:35–56 (1986).

Becker et al., "Production of separation–nozzle systems for uranium enrichment by a combination of x–ray lithography and galvanoplastics," *Naturwissenschaften,* 69:520–523 (1982).

Cload et al., "Development of improved tRNAs for in vitro biosynthesis of proteins containing unnatural amino acids," *Chemistry & Biology,* 3:1033–1038 (1995).

Condra et al., "In vivo emergence of HIV–1 variants resistant to multiple protease inhibitors," *Nature,* 374:569–571 (1995).

Dammer et al., "Specific antigen/antibody interactions measured by force microscopy," *Biophysical Journal,* 70:2437–2441 (1996).

Dawson et al., "Peptide–derived self–assembled monolayers: adsorption of N–stearoly I–Cysteine Methyl Ester on Gold," *Journal of Molecular Recognition,* 10:18–25 (1997).

Duschl et al., "Surface engineering: optimization of antigen presentation in self–assembled monolayers," *Biophysical Journal,* 70:1985–1995 (1996).

Ellman et al., "Biosynthetic method for introducing unnatural amino acids site–specifically into proteins," *Methods in Enzymology,* 202:301–336 (1991).

Geoghegan et al., "Fluorescence–based continuous assay for the asparyl protease of human immunodeficiency virus–1," *FEBS,* 262:119–122 (1990).

Hegner et al., "Ultralarge atomically flat template–stripped Au surfaces for scanning probe microscopy," *Surface Science*, 291:39–46 (1993).

Hegner et al., "Immobilizing DNA on gold via thiol modification for atomic force microscopy imaging in buffer solutions," *FEBS*, 336(3):452–456 (1993).

Hegner et al., "Modified DNA immobilized on bioreactive self–assembled monolayer on gold for dynamic force microscopy imaging in aqueous buffer solution," *J. Vac. Sci. Technol. B*, 14(2):1418–1421 (1996).

Ho et al., "Characterization of human immunodeficiency virus type 1 variants with increased resistance to a $C_2$–symmetric protease inhibitor," *Journal of Virology*, 68:2016–2020 (1994).

Hochuli et al., "Genetic approach to facilitate purification of recombinant proteins with a novel metal chelate adsorbent," *Biotechnology*, 6:1321–1325 (1988).

Kaplan et al., "Selection of multiple human immunodeficiency virus type 1 variants that encode viral proteases with decreased sensitivity to an inhibitor of the viral protease," *Proc. Natl. Acad. Sci. USA*, 91:5597–5601 (1994).

Korant et al., "The HIV protease and therapies for aids," *Advances in Experimental Medicine and Biology*, 421:279–284 (1997).

Linford et al., "Alkyl monolayers on silicon prepared from 1–alkenes and hydrogen–terminated silicon," *J. Am. Chem. Soc.*, 117:3145–3155 (1995).

Loeb et al., "Complete mutagenesis of the HIV–1 protease," *Nature*, 340:397–400 (1989).

Louis et al., "Autoprocessing of the HIV–1 protease using purified wild–type and mutated fusion proteins expressed at high levels in *Escherichia coli*," *Eur. J. Biochem.*, 199:361–369 (1991).

Mrksich et al., "Controlling cell attachment on contoured surfaces with self–assembled monolayers of alkanethiolates on gold," *Proc. Natl. Acad. Sci. USA*, 93:10775–10778 (1996).

Moore et al., "Peptide substrates and inhibitors of the HIV–1 protease," *Biochemical and Biophysical Research Communications*, 159:420–425 (1989).

Nock, "Reversible, site–specific immobilization of polyarginine–tagged fusio proteins on mica surfaces," *FEBS*, 414:233–238 (1997).

Noren et al., "A general method for site–specific incorporation of unnatural amino acids into proteins," *Science*, 244:182–188 (1989).

Prime et al., "Self–assembled organic monolayers: model systems for studying absorption of proteins at surfaces," *Science*, 252:1164–1167 (1991).

Roberts et al., "Rational design of peptide–based HIV proteinase inhibitors," *Science*, 248:358–361 (1990).

Schock et al., "Mutational anatomy of an HIV–1 protease variant conferring corss–resistance to protease inhibitors in clinical trials," *The Journal of Biological Chemistry*, 271:31957–31963 (1996).

Singhvi et al., "Engineering cell shape and function," *Science*, 264:696–698 (1994).

Skalka, "Retroviral proteases: first glimpses at the anatomy of a processing machine," *Cell*, 56:911–913 (1989).

Sundberg et al., "Spatially–addressable immobilization of macromolecules on solid supports," *J. Am. Chem. Soc.*, 117:12050–12057 (1995).

Wagner et al., "ω–functionalized self–assembled monolayers chemisorbed on ultraflat Au(111) surfaces for biological scanning probe microscopy in aqueous buffers," *J. Vac. Sci. Technol. B*, 14(2):1466–1471 (1996).

Wagner et al., "Formation and in Situ modification of monolayers chemisorbed on ultraflat template–stripped gold surfaces," *Langmuir*, 11(10):3867–3875 (1995).

Wagner et al., "Bioreactive self–assembled monolayers on hydrogen–passivated Si(111) as a new class of atomically flat substrates for biological scanning probe microscopy," *Journal of Structural Biology*, 119:189–201 (1997).

Wagner et al., "Covalent immobilziation of native biomolecules onto Au(111) via N–hydroxysuccinimide ester functionalized self–assembled monolayers for scanning probe microscopy," *Biophysical Journal*, 70:2052–2066 (1996).

Weiner et al., "Site–directed mutagenesis of double–stranded DNA by the polymerase chain reaction," *Gene*, 151:119–123 (1994).

Wondrak et al., "Influence of flanking sequences on the dimer stability of human immunodeficiency virus type 1 protease," *Biochemistry*, 35:12957–12962 (1996).

Wu et al., "Structural basis for specificity of retroviral proteases," *Biochemistry*, 37:4518–4526 (1998).

Colliod et al. "Oriented and Covalent Immobilization of Target Molecules to Solid Supports: Synthesis and Application of a Light–Activatable and Thiol–Reactive Cross–Linking Reagent" *Bioconjugate Chem.* 4:528–536 (1993).

Lemmo et al. "Characterization of an Inkjet Chemical Microdispensor for Combinatorial Library Synthesis" Anal. Chem. 69:543–551 (1997).

Marks et al. "By–passing Immunication—Human Antibodies from V–gene Libraries Displayed on Phage"J. Mol. Biol. 222:581–597 (1991).

Pale–Grosdemange et al. "Formation of Self–Assembled Monolayers by Chemisorption of Derivatives of Oligo (ethylene glycol) of Structure $HS(CH_2)_{11}(OCH_2CH_2)_mOH$ on Gold" J. Am. Chem. Soc. 113(1) 12–20 (1991).

Patent Abstract, Patent abstract of Japan (Fuji Film Co Ltd.), Patent Abstracts of Japan, v15(34) (c–0799) Jan. 1991 & JP 02 272081 A (Nov. 1990).

Pham et al. "Human Interleukin–2 Production in Insect (*Trichoplusia ni*) Larvae: Effects and Partial Control of Proteolysis", Biotechnology and Bioengineering, 62(2) 175–182 (1999).

Sigal et al. "A Self–Assembled Monolayer for the Binding and Study of Histidine–Tagged Proteins by Surface Plasmon Resonance", Anal. Chem. 68:490–497 (1996).

Steinnicke et al. Biochemical Characteristics of Caspases–3, –6, –7, and –8* J. Biol. Chem. 272:25719–25723 (1997).

Talanian et al. "Substrate Specificites of Caspase Family Proteases", J. Biol. Chem. 272:9677–9682 (1997).

Thornberry, Nancy A. "Interleukin–1beat Converting Enzyme", Meth. In Enzymology 244:615–631 (1994).

Villa et al. "Caspases and caspase inhibitors", TIBS 22:388–393 (1997).

Wilson et al. "Structure and mechanism of interleukin–1beta converting enzyme" Nature 370:270–275 (1994).

* cited by examiner

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: histidine tag

<400> SEQUENCE: 1

His His His His His His
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: lysine tag

<400> SEQUENCE: 2

Lys Lys Lys Lys Lys Lys
 1               5

<210> SEQ ID NO 3
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: N-dansyl
<220> FEATURE:
<223> OTHER INFORMATION: Description of Artificial Sequence: labeled
      peptide substrate of HIV protease

<400> SEQUENCE: 3

Ser Gln Asn Tyr Pro Ile Val Trp
 1               5
```

MICRODEVICES FOR HIGH-THROUGHPUT SCREENING OF BIOMOLECULES

BACKGROUND OF THE INVENTION

A vast number of new drug targets are now being identified using a combination of genomics, bioinformatics, genetics, and high-throughput (HTP) biochemistry. Genomics provides information on the genetic composition and the activity of an organism's genes. Bioinformatics uses computer algorithms to recognize and predict structural patterns in DNA and proteins, defining families of related genes and proteins. The information gained from the combination of these approaches is expected to boost the number of drug targets, usually proteins, from the current 500 to over 10,000 in the coming decade.

The number of chemical compounds available for screening as potential drugs is also growing dramatically due to recent advances in combinatorial chemistry, the production of large numbers of organic compounds through rapid parallel and automated synthesis. The compounds produced in the combinatorial libraries being generated will far outnumber those compounds being prepared by traditional, manual means, natural product extracts, or those in the historical compound files of large pharmaceutical compares.

Both the rapid increase of new drug targets and the availability of vast libraries of chemical compounds creates an enormous demand for new technologies which improve the screening process. Current technological approaches which attempt to address this need include multiwell-plate-based screening systems, cell-based screening systems, microfluidics-based screening systems, and screening of soluble targets against solid-phase synthesized drug components.

Automated multiwell formats are the best developed high-throughput screening systems. Automated 96-well plate-based screening systems are the most widely used. The current trend in plate-based screening systems is to reduce the volume of the reaction wells further, thereby increasing the density of the wells per plate (96-well to 384-, and 1536-well per plate). The reduction in reaction volumes results in increased throughput, dramatically decreased bioreagent costs, and a decrease in the number of plates which need to be managed by automation.

However, although increases in well numbers per plate are desirable for high throughput efficiency, the use of volumes smaller than 1 microliter in the well format generates significant problems with evaporation, dispensing times, protein inactivation, and assay adaptation. Proteins are very sensitive to the physical and chemical properties of the reaction chamber surfaces. Proteins are prone to denaturation at the liquid/solid and liquid/air interfaces. Miniaturization of assays to volumes smaller than 1 microliter increases the surface to volume ratio substantially. (Changing volumes from 1 microliter to 10 nanoliter increases the surface ratio by 460%, leading to increased protein inactivation.) Furthermore, solutions of submicroliter volumes evaporate rapidly, within seconds to a few minutes, when in contact with air. Maintaining microscopic volumes in open systems is therefore very difficult.

Other types of high-throughput assays, such as miniaturized cell-based assays are also being developed. Miniaturized cell-based assays have the potential to generate screening data of superior quality and accuracy, due to their in vivo nature. However, the interaction of drug compounds with proteins other than the desired targets is a serious problem related to this approach which leads to a high rate of false positive results.

Microfluidics-based screening systems that measure in vitro reactions in solution make use often to several-hundred micrometer wide channels. Micropumps, electroosmotic flow, integrated valves and mixing devices control liquid movement through the channel network. Microfluidic networks prevent evaporation but, due to the large surface to volume ratio, result in significant protein inactivation. The successful use of microfluidic networks in biomolecule screening remains to be shown.

Drug screening of soluble targets against solid-phase synthesized drug components is intrinsically limited. The surfaces required for solid state organic synthesis are chemically diverse and often cause the inactivation or non-specific binding of proteins, leading to a high rate of false-positive results. Furthermore, the chemical diversity of drug compounds is limited by the combinatorial synthesis approach that is used to generate the compounds at the interface. Another major disadvantage of this approach stems from the limited accessibility of the binding site of the soluble target protein to the immobilized drug candidates.

DNA microarray technology is not immediately transferable to protein screening microdevices. To date, microarrays are exclusively available for nucleic acid hybridization assays ('DNA-chips'). Their underlying chemistry and materials are not readily transferable to protein assays. Nucleic acids withstand temperatures up to 100° C., can be dried and re-hydrated without loss of activity and bound directly to organic adhesion layers absorbed on surfaces such as glass. In contrast, proteins must remain hydrated, kept at ambient temperatures, and are very sensitive to the physical and chemical properties of the support materials. Therefore, maintaining protein activity at the liquid-solid interface requires entirely different immobilization strategies than those used for nucleic acids. Additionally, the proper orientation of the protein at the interface is desirable to ensure accessibility of their active sites with interacting molecules.

In addition to the goal of achieving high-throughput screening of compounds against targets to identify potential drug leads, researchers also need to be able to identify a highly specific lead compound early in the drug discovery process. Analyzing a multitude of members of a protein family or forms of a polymorphic protein in parallel enables quick identification of highly specific lead compounds. Proteins within a structural family share similar binding sites and catalytic mechanisms. Often, a compound that effectively interferes with the activity of one family member also interferes with other members of the same family. Using standard technology to discover such additional interactions requires a tremendous effort in time and costs and as a consequence is simply not done.

However, cross-reactivity of a drug with related proteins can be the cause of low efficacy or even side effects in patients. For instance, AZT, a major treatment for AIDS, blocks not only viral polymerases, but also human polymerases, causing deleterious side effects. Cross-reactivity with closely related proteins is also a problem with nonsteroidal anti-inflammatory drugs (NSAIDs) and aspirin. These drugs inhibit cyclooxygenase-2, an enzyme which promotes pain and inflammation. However, the same drugs also strongly inhibit a related enzyme, cyclooxygenase-1, that is responsible for keeping the stomach lining and kidneys healthy, leading to common side-effects including stomach irritation.

For the foregoing reasons, there is a need for miniaturized devices and for methods for the parallel, in vitro, high-throughput screening of functionally and/or structurally related protein targets against potential drug compounds in a manner that minimizes reagent volumes and protein inactivation problems.

SUMMARY OF THE INVENTION

The present invention is directed to a device and methods of use of the device that satisfy the need for parallel, in vitro, high-throughput screening of functionally or structurally related protein targets against potential drug, compounds in a manner that minimizes reagent volumes and protein inactivation problems.

One embodiment of the present invention provides a device that has a plurality of noncontiguous reactive sites and is useful for processing fluid samples. On each of the reactive sites of the device, biological moieties are immobilized on a monolayer via an affinity tag which enhances the site-specific immobilization of the biological moiety onto the monolayer. Each of the reactive sites is separated from neighboring reactive sites by substrate that is free of the monolayer. The monolayer is on, a portion of a surface of a substrate and comprises molecules of the formula X-R-Y where R is a spacer, X is a functional group that binds R to the surface, and Y is a functional group for binding a biological moiety onto the monolayer via the affinity tag. Each of the reactive sites is displayed on the device in a manner that allows it to react with a component of a fluid sample.

In a preferred embodiment the device of the present invention is a micromachined or microfabricated device.

In a particularly preferred embodiment of the device, the plurality of reactive sites are contained within parallel microchannels. These microchannels may be microfabricated into or onto the substrate.

Optionally, at least one coating may be formed on the substrate or applied to the substrate of a device of the present invention such that the coating is positioned between the substrate and the monolayer of each reactive site.

The monolayer of a device of the present invention may optionally be a mixed monolayer of more than one type of organic molecule.

In a preferred embodiment, an adaptor molecule is also included in the device of the present invention to link the affinity tag to the biological moiety.

The affinity tag, biological moiety, and the adaptor molecule (if present) are preferably, but not necessarily, a fusion protein.

The biological moiety immobilized on one reactive site can either be the same as or different from the biological moiety immobilized on a second reactive site. If the reactive sites are different, the biological moieties of the different reactive sites are preferably members of the same protein family or are otherwise functionally or structurally related.

The present invention further provides for methods of using the device to screen a plurality of biological moieties in parallel for their ability to interact with a component of a fluid sample. The interaction being assayed may be a binding interaction or a catalytic one. Some embodiments of these methods first involve delivering the fluid sample to the reactive sites of the device. If binding between the biological moiety and the component is to be detected, the reactive sites are then optionally washed to remove any unbound component from the area. If binding interactions are being monitored, the methods also involve detecting, either directly or indirectly, the retention of the component at each reactive site. If the interaction being assayed is catalytic, then the presence, absence, or amount of reaction product is instead detected.

In other embodiments of the present invention, similar methods are used diagnostically to screen a fluid sample for the presence, absence, or amount of a plurality of analytes (in parallel).

In another method, the device may also be used to screen a plurality of drug candidates in parallel for their ability to bind or react with a biological moiety. In this method, different fluid samples, each containing a different drug candidate (or a different mixture of drug candidates) to be tested, is delivered to the different reactive sites of the invention device.

The present invention also provides for methods of determining in parallel whether or not a plurality of proteins belong to a certain protein family based on either binding to a common ligand or reactivity with a common substrate. These methods involve delivering a fluid sample comprising a ligand or substrate of a known protein family to the reactive sites of the invention device that contain the different proteins and then detecting, either directly or indirectly, for binding or reaction with the known ligand that is characteristic of the protein family.

An alternative embodiment of the invention provides a device for processing a fluid sample that comprises a substrate, a plurality of parallel microchannels microfabricated into or onto said substrates and a moiety immobilized within at least one of the parallel microchannels, in such a way that the moiety interacts with a component of the fluid sample. In a preferred embodiment, the immobilized moiety is a biological moiety such as a protein.

DETAILED DESCRIPTION OF THE INVENTION

Figure 1:
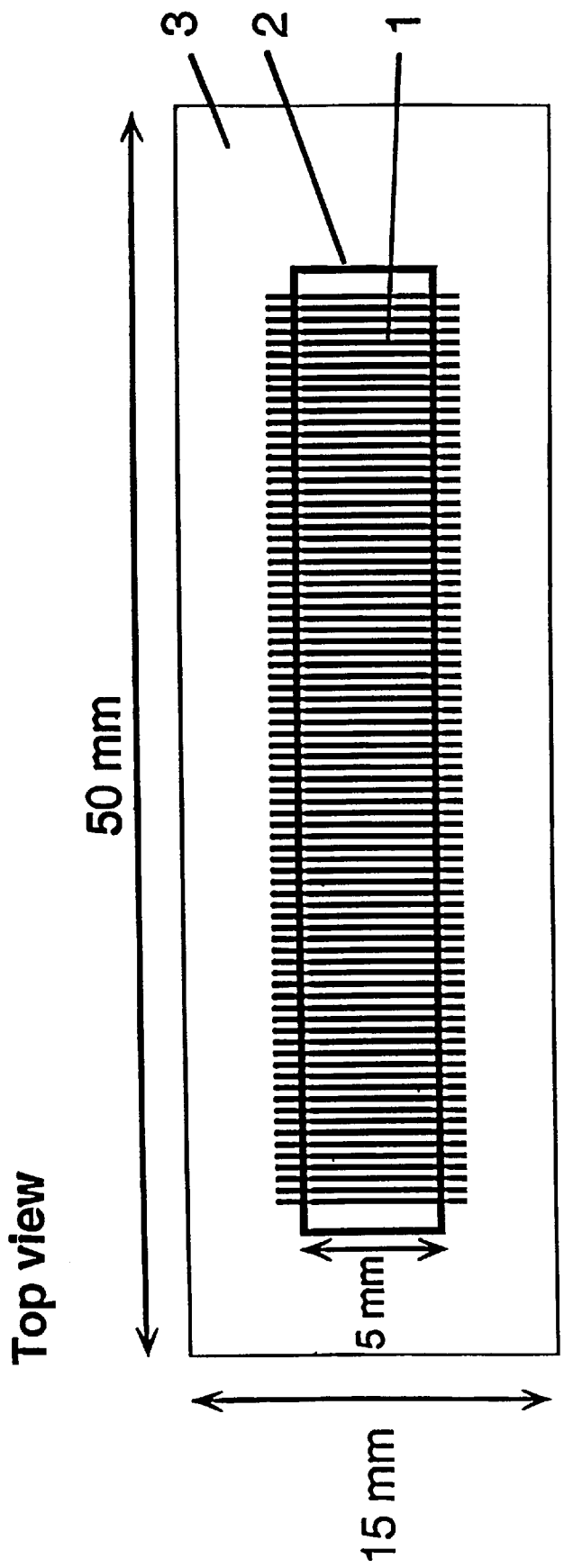
FIG. 1 shows the top view of a covered microchannel array device.

A variety of devices and methods useful for high-throughput drug screening, clinical diagnostics, and related processes are provided by the present invention.

(a) Definitions

The term "substrate" as used herein refers to the bulk, underlying, and core material of the devices of the invention.

The terms "micromachining" and "microfabricating" are both used herein to refer to any number of techniques which are useful in the generation of microstructures (structures of sub-millimeter scale). Such technologies include, but are not limited to, laser ablation, sputtering, electrodeposition, low-pressure vapor deposition, photolithography, and etching. Related technologies such as LIGA (Lithographie, Galvanoformung und Abformtechnik, high aspect ratio plating) are also included. Most of these techniques were originally developed for use in semiconductors, microelectronics, and microelectromechanical systems but are applicable to the present invention as well.

The term "coating" is used herein to refer to a layer that is either formed on or applied to the surface of the substrate. For instance, exposure of a substrate, such as silicon, to air can result in oxidation of the exposed surface. In the case of a substrate made of silicon, a silicon oxide coating is formed on the surface upon exposure to air. In other instances, the coating is in no way derived from the substrate and may be placed upon the surface via mechanical, electrical, or chemical means. An example of this type of coating would be a metal coating that is applied to a polymer substrate. Although a coating may be of any thickness, typically the coating has a thickness smaller than that of the substrate.

An "interlayer" is a second coating or layer that is positioned between the first coating and the substrate. The primary purpose of a typical interlayer is to aid adhesion between the first coating and the substrate. One such example is the use of a titanium interlayer to help attach a gold coating to a silicon chip. However, other possible functions of an interlayer are also anticipated. For instance, some interlayers may perform a role in the detection system of the device.

The term "affinity tag" is used herein to refer to a functional moiety capable of immobilizing a biological moiety onto the exposed functionality of a monolayer. In some cases, the affinity tag may be a simple chemical functional group. Other possibilities include amino acids, polypeptides, proteins, lipid bilayers, or a hydrogel. The affinity tag may be either covalently or noncovalently attached to the biological moiety (via chemical conjugation or as a fusion protein, for instance). In some cases, an affinity tag may also be an internal part of the biological moiety, such as an amino acid. Likewise, the affinity tag may bind to the monolayer either covalently or noncovalently.

An "adaptor molecule", for purposes of this invention, is any entity that links an affinity tag to a biological moiety. The adaptor molecule need not necessarily be a discrete molecule that is noncovalently attached to both the affinity tag and the biological moiety. The adaptor molecule can be covalently attached to the affinity tag or the biological moiety or both (via chemical conjugation or as a fusion protein, for instance). Examples of adaptor molecules include polypeptides, proteins, membrane anchors, and biotin.

A "biological moiety" is any entity that either has, or is suspected of having, a physiological function.

A "monolayer" is a single-molecule thick layer of organic molecules on a surface. A monolayer may be disordered or ordered. One face of the monolayer is composed of chemical functionalities on the termini of the organic molecules that are chemisorbed or physisorbed onto the surface material (headgroups). The other face of the monolayer is exposed and may bear any number of chemical functionalities (end groups). Preferably, the molecules of the monolayer are highly ordered and tightly packed, largely due to hydrophobic and van der Waals interactions between the molecules.

The terms "polypeptide" and "protein" are used interchangeably herein to refer to a polymer of amino acid residues. These terms also apply to amino acid polymers in which one or more amino acid residues is an artificial chemical analogue of a corresponding naturally occurring amino acid, as well as to naturally occurring amino acid polymers. An amino acid polymer in which one or more amino acid residues is an "unnatural" amino acid, not corresponding to any naturally occurring amino acid, is also encompassed by the use of the terms "protein" and "polypeptide" herein.

Proteins are considered herein to be members of the same "protein family" or to be "related" if they show significant similarities in structure and/or function, as would be recognized by one of ordinary skill in the art. Related proteins can be identified by sequence homology searches of DNA and protein databases using standard bioinformatics resources and software packages (examples of public databases: NCBI, NIH, EMBL, SwissProt, Brookhaven database, Washington University—Merck; private databases: Incyte, Hyseq, Human Genome Science; examples of software packages include EMOTIF, Blast, Fasta, Multalign, GCG Wisconsin University). Enzymatically related proteins of non-homologous sequence can be identified by one of ordinary skill in the art by screening the scientific literature (example: Medline database).

The term "fusion protein" refers to a protein composed of two or more polypeptides that, although typically unjoined in their native state, are joined by their respective amino and carboxyl termini through a peptide linkage to form a single continuous polypeptide. It is understood that the two or more polypeptide components can either be directly joined or indirectly joined through a peptide linker/spacer.

The term "nucleic acid" refers to a deoxyribonucleotide or ribonucleotide monomer or polymer in either single- or double-stranded form, and unless otherwise limited, encompasses known analogs of natural nucleotides that can function in a manner similar to naturally occurring nucleotides. The nucleic acid may be obtained from a natural source, an in vitro reaction enzymatic or chemical synthesis. No distinction is made herein between a nucleic acid, a polynucleotide, and an oligonucleotide.

The term "normal physiological condition" is used herein to refer to conditions that are typical inside a living organism or a cell. While it is recognized that some organs or organisms provide extreme conditions, the intra-organismal and intra-cellular environment normally varies around pH 7 (i.e. from pH 6.5 to pH 7.5), contains water as the predominant solvent, and exists at a temperature above 0° C. and below 50° C. It will be recognized that the concentration of various salts depends on the organ, organism, cell, or cellular compartment used as a reference.

(b) Devices with a Plurality of Bioreactive Sites

In one aspect, the present invention provides a device for processing a fluid sample. This device has a plurality of noncontiguous reactive sites, each of the sites comprising the following: a substrate; a monolayer on a portion of a surface of the substrate, comprising molecules of the formula X-R-Y where R is a spacer, X is a functional group that binds R to the surface, and Y is a functional group for binding a biological moiety onto the monolayer; an affinity tag that enhances site-specific immobilization of a biological moiety onto the monolayer; and a biological moiety immobilized on the monolayer through Y via the affinity tag.

Each of the sites of the device may independently react with a component of the fluid sample and are separated from each other by substrate that is free of monolayer molecules of the formula X-R-Y.

Numerous different materials may be used as the substrate of the invention device. The substrate may be organic or inorganic, biological or non-biological, or any combination of these materials. The substrate can optionally be transparent or translucent. Substrates suitable for micromachining or microfabrication are preferred. The substrate of the invention can optionally comprise a material selected from a group consisting of silicon, silica, quartz, glass, controlled pore glass, carbon, alumina, titanium dioxide, germanium, silicon nitride, zeolites, and gallium arsenide. Many metals such as gold, platinum, aluminum, copper, titanium, and their alloys are also options for substrates. In addition, many ceramics and polymers may be used as substrates, either in planar or bead form. Polymers which may be used as substrates include, but are not limited to, the following: polystyrene; poly(tetra)fluorethylene; (poly) vinylidenedifluoride; polycarbonate; polymethylmethacrylate; polyvinylethylene; polyethyleneimine; poly(etherether) ketone; polyoxymethylene (POM); polyvinylphenol; polylactides; polymethacrylimide (PMI); polyalkenesulfone (PAS); polyhydroxyethylmethacrylate; polydimethylsiloxane; polyacrylamide; polyimide; co-block-polymers; and Eupergit®. Photoresists, polymerized Langmuir-Blodgett films, and LIGA structures may also serve as substrates in the present invention. The preferred substrates of the present invention comprise silicon, silica, glass, or a polymer.

In a preferred embodiment of the present invention the device comprises a micromachined or microfabricated device. The device is optionally a microdevice with dimensions on the millimeter to centimeter scale.

In a preferred embodiment of the invention, each of the reactive sites of the device is in a microchannel oriented parallel to microchannels of other reactive sites on the device. The microchannels of such a device have optionally been microfabricated or micromachined into or onto the substrate of the device. FIG. 1 illustrates one embodiment of the invention showing an array of microchannels 1 that have been fabricated into a bulk substrate material. In the particular device shown, eighty parallel microchannels 1 have been microfabricated into a substrate 3.

In one embodiment of the invention, the device comprises at least 2 parallel microchannel reactive sites. In another embodiment of the invention, the device comprises at least 10 parallel microchannel reactive sites. In a preferred embodiment of the invention, the device comprises at least 100 parallel microchannel reactive sites. In a particularly preferred embodiment, the device comprises from about 100 to about 500 parallel microchannels. The microchannels are typically separated from one another by from about 10 $\mu$m to about 5 mm. The device may optionally comprise from about 2 to about 500 parallel microchannels per cm$^2$ of substrate.

The dimensions of the microchannels may vary. However, in preferred embodiments the scale is small enough so as to only require minute fluid sample volumes. The width and depth of each microchannel of the invention device is typically between about 10 $\mu$m and about 500 $\mu$m. In a preferred embodiment of the device, the width and depth of each microchannel is between about 50 and 200 $\mu$m. The length of each microchannel is from about 1 to about 20 mm in length. In a preferred embodiment, the length of each microchannel is from about 2 to about 8 mm long. Any one of a variety of channel cross-section geometries (trapezoidal, rectangular, v-shaped, semicircular, etc.) may be employed in the device. The geometry is determined by the type of microfabrication or micromachining process used to generate the microchannels, as is known in the art. Trapezoidal or rectangular cross-section geometries are preferred for the microchannels, since they readily accommodate standard fluorescence detection methods.

In order to generate a plurality of reactive sites, such as a parallel array of microchannels, the substrate material first has to be cleaned to remove contaminants such as solvent stains, dust, or organic residues. A variety of cleaning procedures can be used depending on the substrate material and origin of contaminants. These include wet immersion processes (for example, RCA1+2, "pyranha", solvents), dry vapor phase cleaning, thermal treatment, plasma or glow discharge techniques, polishing with abrasive compounds, short-wavelength light exposure, ultrasonic agitation and treatment with supercritical fluids.

Channels can then be formed on the surface of the substrate by either (1) bulk micromachining, (2) sacrificial micromachining, (3) LIGA (high aspect ratio plating) or (4) other techniques, or any combination thereof. Such techniques are well known in the semiconductor and microelectronics industries and are described in, for example, Ghandi, *VLSI Fabrication Principles*, Wiley (1983) and Sze, *VLSI, Technology*, 2nd. Ed., McGraw-Hill (1988); Wolf and Taube, *Silicon Processing for the VLSI Era, Vol.* 1, Lattice Press (1986), and Madou, *Fundamentals of Microfabrication*, CRC Press (1997).

In bulk micromachining, large portions of the substrate are removed to form rectangular or v-shaped grooves comprising the final dimensions of the microchannels. This process is usually carried out with standard photolithographic techniques involving spin-coating of resist materials, illumination through lithography masks followed by wet-chemical development and posttreatment steps such as descumming and post-baking. The resulting resist pattern is then used as an etch resist material for subsequent wet or dry etching of the bulk material to form the desired topographical structures. Typical resist materials include positive and negative organic resists (such as Kodak 747, PR102), inorganic materials (such as polysilicon, silicon nitride) and biological etch resists (for example Langmuir-Blodgett films and two-dimensional protein crystals such as the S-layer of *Sulfolobus acidocladarius*). Pattern transfer into the substrate and resist stripping occurs via wet-chemical and dry etching techniques including plasma etching, reactive ion etching, sputtering, ion-beam-assisted chemical etching and reactive ion beam etching.

In one embodiment of the invention, for instance, a photoresist may be spincoated onto a cleaned 4 inch Si(110) wafer. Ultraviolet light exposure through a photomask onto the photoresist then results in a pattern of channels in the photoresist, exposing a pattern of strips of the silicon underneath. Wet-chemical etching techniques can then be applied to etch the channel pattern into the silicon. Next, a thin layer of titanium can be coated on the surface. A thin layer of gold is then coated on the surface via thermal or electron beam evaporation. Standard resist stripping follows. (Alternatively, the gold-coating could be carried out after the strip resist.)

Figure 2:
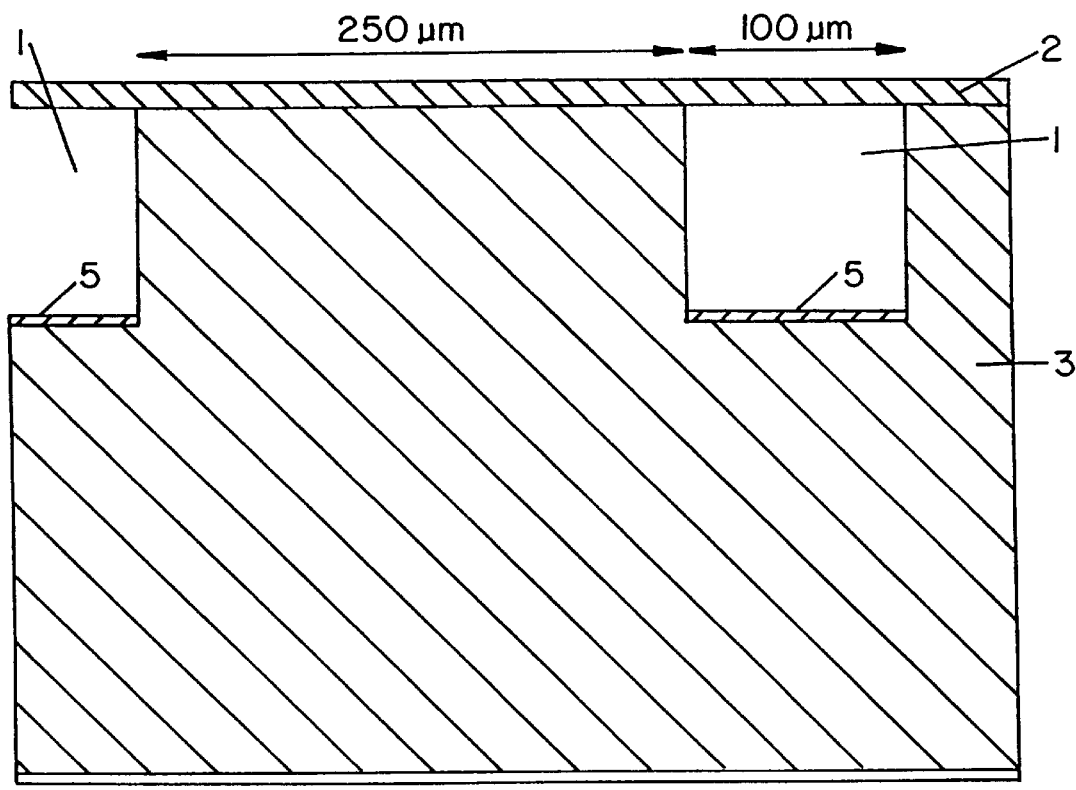
FIG. 2 shows a cross section of a covered microchannel array fabricated by bulk micromachining.

FIG. 2 shows a cross section view of one example of a microchannel array fabricated by bulk micromachining. A microchannel 1 in substrate 3 is covered by a glass cover 2. At the bottom of the microchannel, the surface of the substrate 3 is covered with a coating 5.

In sacrificial micromachining, the substrate is left essentially untouched. Various thick layers of other materials are built up by vapor deposition, plasma-enhanced chemical vapor deposition (PECVD) or spin coating and selectively remain behind or are removed by subsequent processing steps. Thus, the resulting channel walls are chemically different from the bottom of the channels and the resist material remains as part of the microdevice. Typical resist materials for sacrificial micromachining are silicon nitride ($Si_3N_4$), polysilicon, thermally grown silicon oxide and organic resists such as SU-8 and polyimides allowing the formation of high aspect-ratio features with straight sidewalls.

Figure 3:
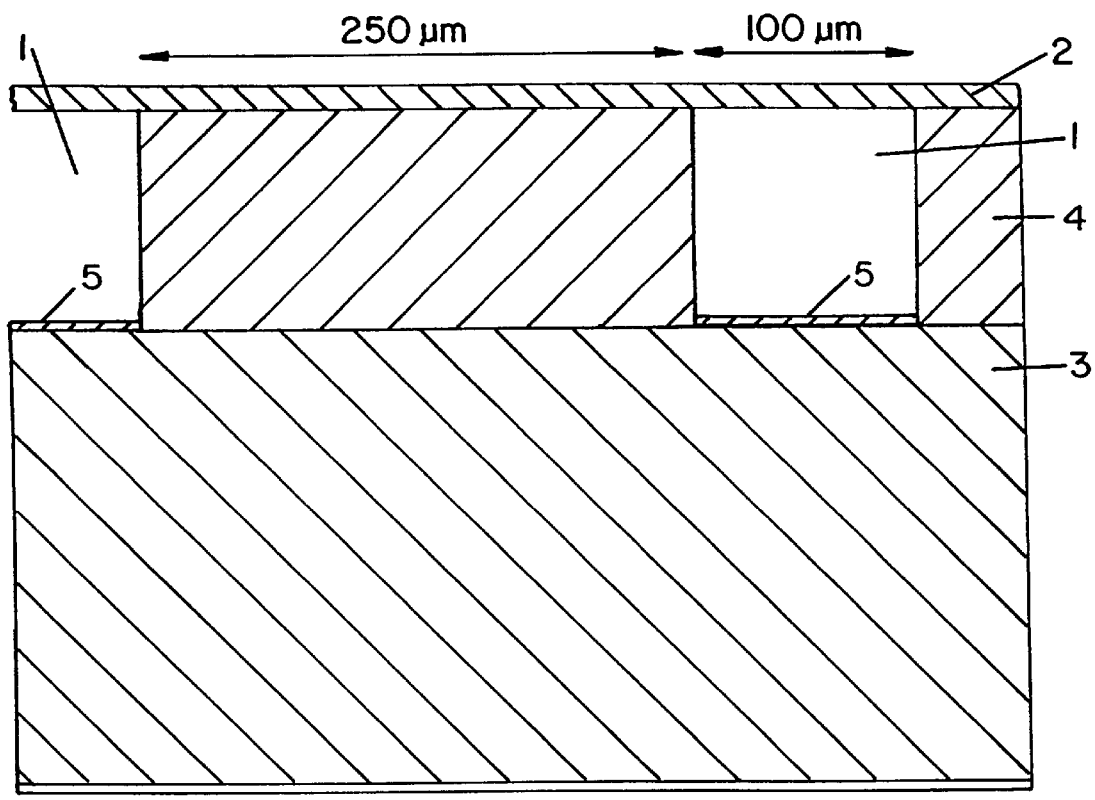
FIG. 3 shows a cross section of a covered microchannel array fabricated by sacrificial micromachining.

FIG. 3 shows a cross section view of one example of a microchannel array that has been fabricated by sacrificial micromachining. Microchannel 1 has walls that consist of photoresist 4 and a floor that comprises a substrate 3 that is covered with a coating 5.

In high-aspect ratio plating or LIGA, three-dimensional metal-structures are made by high-energy X-ray radiation exposures on materials coated with X-ray resists. Subsequent electrodeposition and resist removal result in metal structures that can be used for precision plastic injection molding. These injection-molded plastic parts can be used either as the final microdevice or as lost molds. The LIGA process has been described by Becker et al., *Microelectron Engineering* (1986) 4:35–56 and Becker et al., *Naturwissenschaften* (1982) 69:520–523.

Alternative techniques for the fabrication of microchannel arrays include focused ion-beam (FIB) milling, electrostatic discharge machining (EDM), ultrasonic drilling, laser ablation (U.S. Pat. No. 5,571,410), mechanical milling and thermal molding techniques. One skilled in the art will recognize that many variations in microfabrication or micromachining techniques may be used to construct the device of the present invention.

In one embodiment, transparent or translucent covers are attached to the substrate via anodic bonding or adhesive coatings, resulting in microchannel arrays with inlet and outlet ports. In a preferred embodiment, the microchannel covers are glass, especially Pyrex or quartz glass. In alternative embodiments, a cover which is neither transparent nor translucent may be bonded or otherwise attached to the substrate to enclose the microchannels. In other embodiments the cover may be part of a detection system to monitor the interaction between biological moieties immobilized within the channel and an analyte. Alternatively, a polymeric cover may be attached to a polymeric substrate channel array by other means, such as by the application of heat with pressure or through solvent-based bonding.

One particular embodiment of a covered microchannel array is illustrated by FIG. 1. In this device, a transparent glass cover 2 covers most of the length, although not all, of each of the parallel microchannels of the array. Since in this particular embodiment the microchannels do not extend fully to the edge of the substrate, the incomplete coverage of the channel length provides an inlet and outlet port for each of the microchannels.

Attachment of the covers to the microchannel array can precede monolayer formation. If this is the case, then the monolayer component containing solution (typically an organic solvent) can be applied to the interior of the channels via microfabricated dispensing systems that have integrated microcapillaries and suitable entry/exit ports. Alternatively, the monolayers can be deposited in the microchannels prior to enclosure of the microchannels. For these embodiments, monolayers can optionally be transferred to the inner microchannel surfaces via simple immersion or through microcontact printing (see PCT Publication WO 96/29629).

The volume of each enclosed microchannel may optionally be from about 5 nanoliters to about 300 nanoliters. In a preferred embodiment, the volume of an enclosed microchannel of the invention device is between 10 and 50 nanoliters.

Volumes of fluid may be moved through each microchannel by a number of standard means known to those skilled in the art. The sophisticated means required for moving fluids through microfluidic devices and mixing in microtiter plates are not needed for the microchannel array of the present invention. Simple liquid exchange techniques commonly used with capillary technologies will suffice. For instance, fluid may be moved through the channel using standard pumps. Alternatively, more sophisticated methods of fluid movement through the microchannels such as electro-osmosis may be employed (for example, see U.S. Pat. No. 4,908,112).

In one embodiment of the present invention, bulk-loading dispensing devices can be used to load all microchannels of the device at once with the same fluid. Alternatively, integrated microcapillary dispensing devices may be microfabricated out of glass or other substrates to load fluids separately to each microchannel of the device.

After formation of a microchannel, the sides bottom, or cover of the microchannel or any combination thereof, can then be further chemically modified to achieve the desired bioreactive and biocompatible properties.

The reactive sites of the device may optionally further comprise a coating between a substrate and its monolayer. This coating may either be formed on the substrate or applied to the substrate. The substrate can be modified with a coating using thin-film technology based on either physical vapor deposition (PVD) or plasma-enhanced chemical vapor deposition (PECVD). Thin layers of metals or the exposure of hydroxylated surfaces on a substrate are often necessary to allow chemisorption or physisorption of bioreactive organic monolayer systems. Alternatively, plasma exposure can be used to directly activate the substrate. For instance, plasma etch procedures can be used to oxidize a polymeric surface (i.e. polystyrene or polyethylene) to expose polar functionalities such as hydroxyls, carboxylic acids, aldehydes, or the like on the surface.

The coating on the substrate may comprise a metal film. Possible metal films include, but are not limited to aluminum, chromium, titanium, nickel, stainless steel, zinc, lead, iron, magnesium, manganese, cadmium, tungsten, cobalt, and alloys or oxides thereof. In a preferred embodiment, the metal film is a noble metal film. Noble metals that may be used for a noble metal film include, but are not limited to gold, platinum, silver, copper, and palladium. In an especially preferred embodiment, the coating comprises gold or a gold alloy. In a preferred embodiment, the metal film is from about 50 nm to about 500 nm in thickness.

In alternative embodiments, the coating on the substrate comprises a composition such as silicon, silicon oxide, silicon nitride, silicon hydride, indium tin oxide, magnesium oxide, alumina, glass, hydroxylated surfaces, or a polymer.

If the reactive site comprises a coating between the substrate and the monolayer, then it is understood that the coating must be composed of a material for which a suitable functional group X is available (see below). If no such coating is present, then it is understood that the substrate must be composed of a material for which a suitable functional group X is available.

It is contemplated that many coatings will require the addition of at least one adhesion layer or mediator between said coating and said substrate. For instance, a layer of titanium may be desirable between a silicon wafer substrate and a gold coating. In an alternative embodiment an epoxy glue such as Epo-tek 377® and Epo-tek 301-2® (Epoxy Technology Inc., Billerica, Mass.) may be preferred to aid adherence of the coating to the substrate. Determinations as to what material should be used for the adhesion layer would be obvious to one skilled in the art once materials were chosen for the substrate and coating. In other embodiments, additional adhesion mediators or interlayers may be necessary to improve the mechanical or optical properties of the device, for example, for detection purposes in waveguides.

Deposition or formation of the coating on the substrate (if such coatings are desired) must occur prior to the formation of bioreactive monolayers thereon.

The monolayer of each reactive site is comprised of molecules of the general formula X-R-Y where R is a spacer, X is a functional group that binds R to the surface of a portion of the substrate, and Y is a functional group for binding a biological moiety onto the monolayer. Three major classes of monolayer formation are preferably used to expose high densities of bioreactive omega-functionalities on the substrate: (i) alkylsiloxane monolayers ("silanes") on hydroxylated surfaces (as taught in, for example, U.S. Pat. No. 5,405,766, PCT Publication WO 96/38726, U.S. Pat. No. 5,412,087, and U.S. Pat. No. 5,688,642); (ii) alkyl-thiol/dialkyldisulfide monolayers on noble metals (preferably Au(111)) (as, for example, described in Allara et al., U.S. Pat. No. 4,690,715; Bamdad et al., U.S. Pat. No. 5,620,850; Wagner et al., *Biophysical Journal*, 1996, 70:2052–2066); and (iii) alkyl monolayer formation on oxide-free passivated silicon (as taught in, for example, Linford et al., *J. Am. Chem. Soc.*, 1995, 117:3145–3155, Wagner et al., *Journal of Structural Biology*, 1997, 119:189–201, and U.S. Pat. No. 5,429,708). One of ordinary skill in the art, however, will recognize that many possible moieties may be substituted for X, R, and/or Y, dependent largely upon the choice of substrate, coating, and affinity tag. Many examples of monolayers are described in Ulman, *An Introduction to Ultrathin Organic Films: From Langmuir-Blodgett to Self-Assembly*, Academic Press (1991), herein incorporated by reference.

R of the monolayer molecule may comprise a hydrocarbon chain from about 1 to about 200 carbons long. The hydrocarbon chain may comprise an alkyl, aryl, alkenyl, alkynyl, cycloalkyl, alkaryl, aralkyl group, or any combination thereof. In a preferred embodiment, R is a chemical moiety that promotes formation of a self-assembled monolayer. In a preferred embodiment, R is an alkylchain from about 8 to about 22 carbons long. In a further preferred embodiment, R is a straight alkane from about 8 to about 22 carbons long. However, it is also contemplated that in an alternative embodiment, R may readily comprise a hydrocarbon chain from about 2 to about 200 carbons long and interrupted by at least one hetero atom. The interrupting hetero groups can include —O—, —CONH—, —CONHCO—, —NH—, —CSNH—, —CO—, —CS—, —S—, —SO—, —(OCH$_2$CH$_2$)$_n$— (where n=1–20), —(CF$_2$)$_n$— (where n=1–22), and the like. Alternatively, one or more of the hydrogen moieties of R can optionally be substituted with deuterium.

X may be chosen as any group which affords chemisorption or physisorption of the monolayer onto the surface of the substrate (or the coating, if present). For instance, if the substrate or coating is a metal or metal alloy, X, at least prior to incorporation into the monolayer, is preferably an asymmetrical or symmetrical disulfide, sulfide, diselenide, selenide, thiol, isonitrile, selenol, a trivalent phosphorus compound, isothiocyanate, isocyanate, xanthanate, thiocarbamate, a phosphine, a amine, thio acid or dithio acid. This embodiment is especially preferred when the substrate, or coating if used, is a noble metal such as gold, silver, or platinum.

If the substrate of the device is a material such as silicon, silicon oxide, indium tin oxide, magnesium oxide, alumina, quartz, glass, or silica, then a preferred embodiment of the invention comprises an X that, prior to incorporation into said monolayer, is a monohalosilane, dihalosilane, trihalosilane, trialkoxysilane, dialkoxysilane, or a monoalkoxysilane. Among these silanes, trichlorosilane and trialkoxysilane are particularly preferred.

In other embodiments, the surface of the substrate (or coating thereon) is composed of a metal oxide such as titanium oxide, tantalum oxide, indium tin oxide, magnesium oxide, or alumina and X is a carboxylic acid. Alternatively, if the surface of the substrate (or coating thereon) of the device is copper, then X may optionally be a hydroxamic acid.

If the substrate used in the invention is a polymer, then in many cases a coating on the substrate such as a copper coating will be included in the device. An appropriate functional group X for the coating would then be chosen for use in the device. In an alternative embodiment comprising a polymer substrate, the surface of the polymer may be plasma-modified to expose desirable surface functionalities for monolayer formation. For instance, EP 780423 describes the use of a monolayer molecule that has an alkene X functionality on a plasma exposed surface. Still another possibility for the invention device comprised of a polymer is that the surface of the polymer on which the monolayer is formed is functionalized due to copolymerization of appropriately functionalized precursor molecules.

Another possibility is that prior to incorporation into the monolayer, X can be a free-radical-producing moiety. This functional group is especially appropriate when the surface on which the monolayer is formed is a hydrogenated silicon surface. Possible free-radical producing moieties include, but are not limited to, diacylperoxides, peroxides, and azo compounds. Alternatively, unsaturated moieties such as unsubstituted alkenes, alkynes, cyano compounds and isonitrile compounds can be used for X, if the reaction with X is accompanied by ultraviolet, infrared, visible, or microwave radiation.

In alternative embodiments, X, prior to incorporation into the monolayer, may be a hydroxyl, carboxyl, vinyl, sulfonyl, phosphoryl, silicon hydride, or an amino group.

The component, Y, of the monolayer is responsible for binding a biological moiety onto the monolayer. In a preferred embodiment of the invention, the Y group is either highly reactive (activated) towards the biological moiety or is easily converted into such an activated form. In a preferred embodiment, the coupling of Y with the biological moiety occurs readily under normal physiological conditions not detrimental to the biological activity of the biological moiety. One skilled in the art will also appreciate that in many cases, the functional group Y will be altered upon interacting with the biological moiety. Although the functional group Y may either form a covalent linkage or a noncovalent linkage with the biological moiety a covalent linkage is preferred.

In one embodiment of the present invention, Y is a functional group that is activated in situ before attachment of the biological moiety's affinity tag. Possibilities for this type of functional group include, but are not limited to, such simple moieties such as a hydroxyl, carboxyl, amino, aldehyde, carbonyl, methyl, methylene, alkene, alkyne, carbonate, aryliodide, or a vinyl group. Appropriate modes of activation for these simple functional groups would be known by one of ordinary skill in the art. Alternatively, Y can comprise a functional group that requires photoactivation prior to becoming activated enough to trap the biological moiety.

In an especially-preferred embodiment of the device of the present invention, Y is a highly reactive functional moiety compatible with monolayer formation and needs no in situ activation prior to reaction with the biological moiety or its affinity tag. Such possibilities for Y include, but are not limited to, maleimide, N-hydroxysuccinimide (Wagner et al., *Biophysical Journal*, 1996, 70:2052–2066), nitrilotriacetic acid (U.S. Pat. No. 5,620,850), activated hydroxyl, haloacetyl, bromoacetyl, iodoacetyl, activated carboxyl, hydrazide, epoxy, aziridine, trifluoromethyldiaziridine, pyridyldisulfide, N-acyl-imidazole, imidazolecarbamate, succinimidylcarbonate, arylazide, anhydride, diazoacetate, benzophenone, isothiocyanate, isocyanate, imidoester, fluorobenzene, and biotin.

Figure 4:
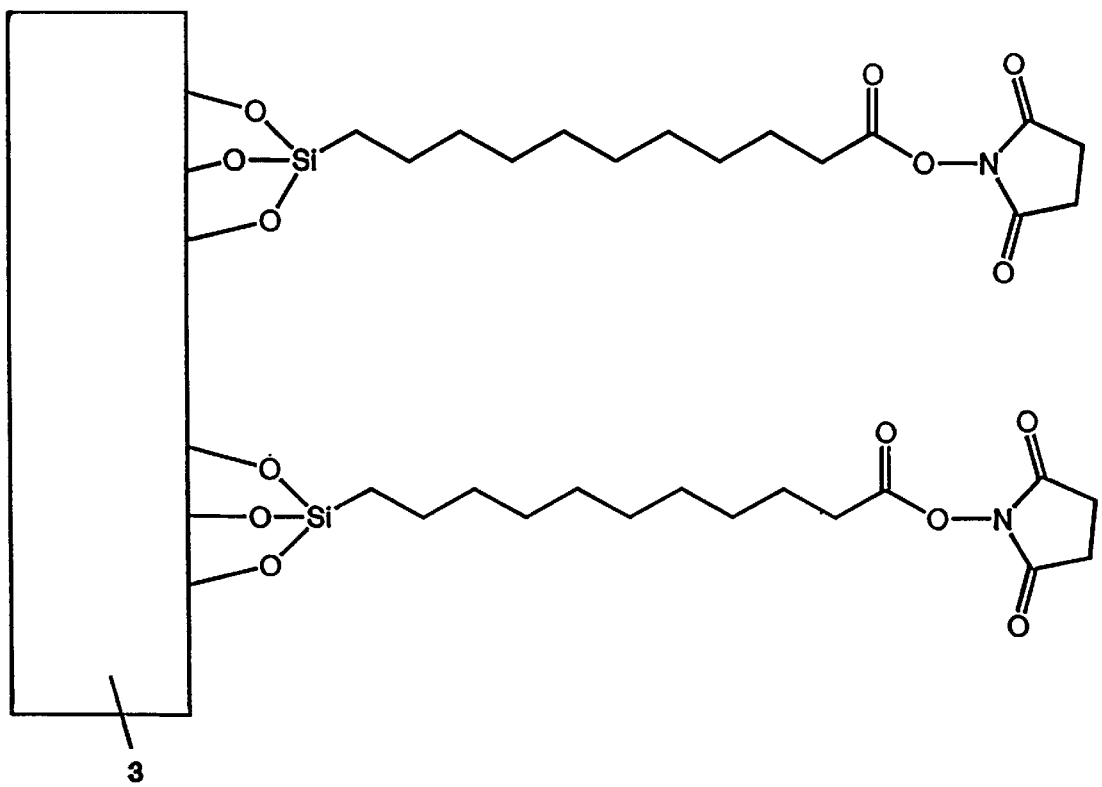
FIG. 4 shows aminoreactive monolayer molecules on a substrate.

FIG. 4 shows one example of a monolayer on a substrate 3. In this example, substrate 3 comprises silicon (having a silicon oxide surface). The monolayer is aminoreactive because it bears a functional group Y that is N-hydroxysuccinimide.

Figure 5:
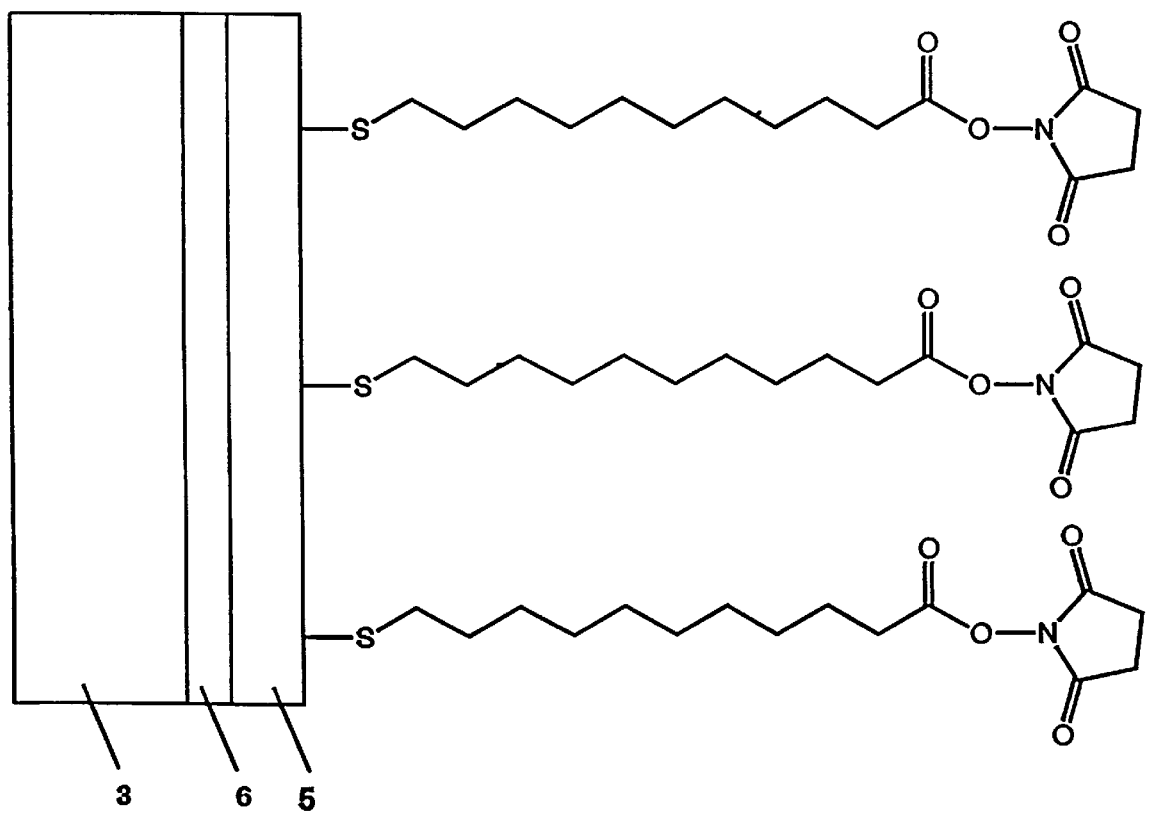
FIG. 5 shows aminoreactive monolayer molecules on a coated substrate.

FIG. 5 shows another example of a monolayer on a substrate 3. In this case, however, a thin film coating 5 comprised of gold covers the surface of the substrate 3. Also, in this embodiment, an adhesion interlayer 6 is used to adhere the coating 5 to the substrate 3 and is comprised of titanium. This monolayer is also aminoreactive because it bears a functional group Y that is N-hydroxysuccinimide.

In an alternative embodiment, Y is selected from the group of simple functional moieties. Possible Y functional groups include, but are not limited to, —OH, —NH$_2$, —COOH, —COOR, —RSR, —PO$_4^{-3}$, OSO$_3^{-2}$, —SO$_3$, —COO—, —SOO—, —CONR$_2$, —CN, —NR$_2$, and the like. Simple groups such as these are only preferred for X when the affinity tag of the invention composes a layer of affinity tag molecules (such as poly-lysine) that coats the exposed portion of the monolayer prior to immobilization of the biological moiety (see below).

The monolayer molecules of the present invention can optionally be assembled on the surface in parts. In other words, the monolayer need not necessarily be constructed by chemisorption or physisorption of molecules of the formula X-R-Y to the surface of the substrate (or coating). Instead, in one embodiment, X may be chemisorbed or physisorbed to the surface of the substrate (or coating) alone first. Then, R or even just individual components of R can be attached to X through a suitable chemical reaction. Upon completion of addition of the spacer R to the X moiety already immobilized on the surface, Y can be attached to the ends of the monolayer molecule through a suitable covalent linkage.

Not all monolayer molecules at a given reactive site need to be identical. Some may consist of mixed monolayers. For instance, the monolayer of an individual reactive site may optionally comprise at least two different X-R-Y molecules. This second X-R-Y molecule may immobilize the same or a different biological moiety. In addition, many of the monolayer molecules, X-R-Y, of a reactive site may have failed to attach any biological moiety.

As another alternative of the invention, the monolayer of an individual reactive site can comprise a second organic molecule that is of the formula, X-R-V where R is the spacer, X is the functional group that binds R to the surface, and V is a moiety resistant to the non-specific binding of biomolecules. One of ordinary skill in the art will recognize that the possibilities for V will vary depending upon the nature of the biological moiety chosen for the sites of the device. For instance, functional groups V which are resistant to non-specific protein binding are used if the immobilized biological moiety of the device comprises protein. The nature of V will be somewhat dependent upon the type of proteins and solutions used. However, V will most typically comprise a hydroxyl, saccharide, or polyethylene glycol moiety (EP Publication 780423).

As a still further alternative of the invention device, the device may further comprise at least one unreactive site devoid of any biological moiety that comprises a monolayer of molecules of the formula X-R-V, where R is the spacer, X is the functional group that binds R to the surface, and V is the moiety resistant to the non-specific binding of biomolecules. In this embodiment, the unreactive site does not comprise any monolayers of molecules of the formula X-R-Y.

Regardless of the nature of the monolayer molecules, in some cases it can be desirable to provide crosslinking between molecules of the monolayer. In general, this confers additional stability to the monolayer. Methods of crosslinking such monolayers are known to those skilled in the art (see Ullman, *An Introduction to Ultrathin Organic Films: From Langmuir-Blodgett to Self-Assembly*, Academic Press (1991).

In addition to facilitating binding of the biological moiety to the substrate, fuctionalization of the substrate with monolayers is necessary for other reasons as well. Many biological moieties and protein, in particular, are susceptible to disruption of their bioactivities at surface interfaces. Proteins are prone to both denaturation and undesirable, non-specific binding at the solid/liquid interface. Other biological moieties such as small molecule ligands may have less problematic interactions with the substrate surface interface, but upon approach of the biological binding partner, presumably a protein, to the small molecule in an assay, problems of inactivation become highly relevant. A highly ordered organic monolayer effectively "carpets" the surface of the substrate or coating, protecting the biological moiety from contact with the surface. These highly-ordered, self-assembled monolayers are preferred in the present invention. Additionally, the spacer R creates distance between the immobilized biological moiety and the surface.

Following formation of monolayers on the reactive sites of the invention device, the biological moieties are immobilized on the monolayers via the affinity tags. A solution containing the biological moiety to be immobilized can be exposed to the bioreactive units of the microdevice by either dispensing the solution by means of microfabricated adapter systems with integrated microcapillaries and entry/exit ports or alternatively by transferring the biological moieties via noncontact printing using dispensing microdevices with ball-point pen-type of mechanisms. The use of other printing techniques is also anticipated. Following attachment of the biological moieties to the monolayer, unreacted Y-functional groups preferably quenched prior to use of the device.

The affinity tag is of critical importance to the present invention. The use of an affinity tag on the biological moiety of interest to be immobilized, allows for at least one of two advantages. An affinity tag can confer enhanced binding or reaction with Y. This enhancement effect may be either kinetic or thermodynamic. In general, affinity tag/Y-group combination used in the present invention preferably allows for immobilization of the biological molecule in a manner which does not require harsh conditions. This helps ensure that the biological reactivity of the biological moiety remains intact. Aqueous, biological buffer conditions are ideal. An affinity tag can also offer immobilization that is specific to a designated site or location on the biological moiety. This site-specific immobilization will help ensure that the reactive site of the biological moiety is accessible to ligands in solution.

In a preferred embodiment, especially when the biological moiety of the invention device is a protein or a polypeptide, the affinity tag comprises at least one amino acid. The affinity tag may be a polypeptide comprising at least one monolayer-reactive amino acid. Alternatively, the affinity tag may be a lone, monolayer-reactive amino acid. Examples of possible monolayer-reactive amino acids include cysteine, lysine, histidine, arginine, tyrosine, and glutamine. A polypeptide or single amino acid affinity tag is preferably expressed as a fusion protein along with the biological moiety. Amino acid tags provide either a single amino acid or a series of amino acids that can interact with the Y-functionalities of the monolayer. Amino acid affinity tags can also be introduced to a specific site on a recombinant protein to facilitate oriented immobilization by covalent binding to the bioreactive Y-functional group of the monolayer.

The affinity tag may comprise a poly(amino acid) tag. A poly(amino acid) tag is a polypeptide that comprises from about 2 to about 100 residues of a single amino acid. Other amino acid residues may also be present in the affinity tag. For instance, the affinity tag may comprise a poly-cysteine, poly-lysine, poly-arginine, or poly-histidine. Amino acid tags are preferably composed of two to twenty residues of a single amino acid, such as, for example, histidines, lysines, arginines, cysteines, glutamines, tyrosines, or any combination of these. According to a preferred embodiment, an amino acid tag of one to twenty amino acids includes at least one to ten cysteines for thioether linkage; or one to ten lysines for amide linkage; or one to ten arginines for coupling to vicinal dicarbonyl groups. One of ordinary skill in the art can readily pair suitable affinity tags with a given Y-functionality.

The position of the amino acid tag can be at the amino-, or carboxy-terminus of the protein or anywhere in-between. Where compatible with protein function, affinity tags introduced for protein purification are preferentially located at the C-terminus of the recombinant protein to ensure that only full-length proteins are isolated during protein purification.

Affinity tags may also contain one or more unnatural amino acids. Unnatural amino acids can be introduced using suppressor tRNAs that recognize stop codons (i.e. amber), as described in Noren et al., *Science*, 1989, 244:182–188, Ellman et al., *Methods Enzym.*, 1991, 202:301–336, and Cload et al., *Chem. Biol.*, 1996, 3:1033–1038, herein incorporated by reference. The tRNAs are chemically aminoacylated to contain chemically altered ("unnatural") amino acids for use with specific coupling chemistries (i.e. ketone modifications, photoreactive groups).

In an alternative embodiment the affinity tag can comprise a whole protein, such as, but not limited to, glutathione S-transferase, an antibody, avidin, or streptavidin.

Other bioconjugation and immobilization techniques known in the art may be adapted for the purpose of immobilizing biomolecules on activated monolayers. For instance, in an alternative embodiment, the affinity tag may be an organic bioconjugate which is chemically coupled to the biomolecule of interest. Biotin or an antigen may be chemically crosslinked to the biomolecule. Alternatively, a chemical crosslinker may be used that attaches a simple functional moiety such as a thiol or an amine to the biomolecule.

Figure 6:
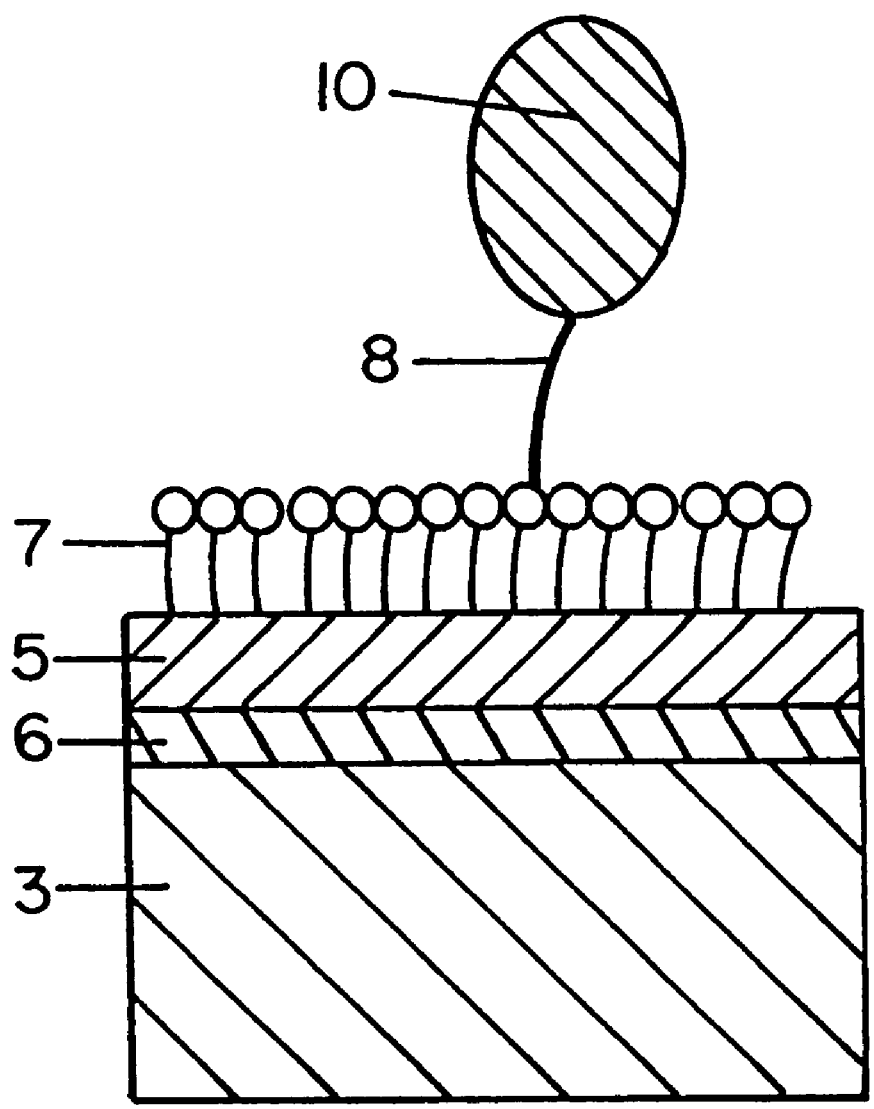
FIG. 6 shows a biological moiety immobilized on a monolayer-coated substrate via an affinity tag.

FIG. 6 shows a biological moiety 10 immobilized on a monolayer 7 on a substrate 3. An affinity tag 8 connects the biological moiety 10 to the monolayer 7. The monolayer 7 is formed on a coating 5 separated from the surface of the substrate 3 by an interlayer 6.

Figure 7:
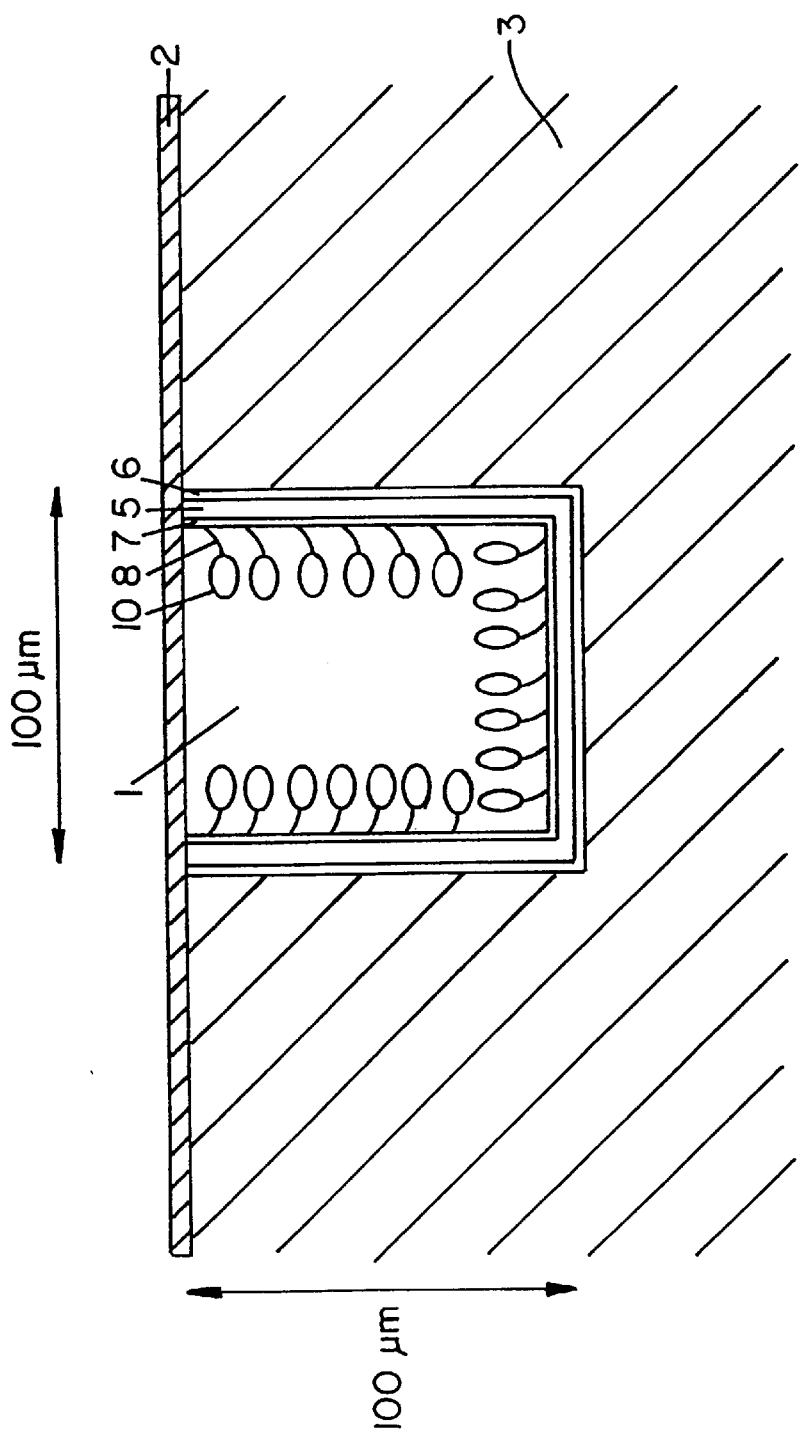
FIG. 7 shows a cross section view of a biomolecule-coated microchannel in a microchannel array device.

FIG. 7 shows a cross section of a biomolecule-coated microchannel of one embodiment of a microchannel array device. The microchannel 1 is covered by a glass cover 2. The walls of the microchannel are comprised of substrate 3, coated first with an interlayer 6, then with a coating 5, then with an organic monolayer 7 and finally, with the biological moiety 10 via the affinity tag 8.

In an alternative embodiment, the affinity tag is a component of a layer of affinity tag molecules immobilized on the monolayer. A hydrogel can serve as a suitable layer of affinity tag molecules. Dextran is one possible hydrogel material useful for the present invention. Alternatively, other polysaccharides or water-swellable organic polymers may also suffice. Uses of such hydrogels to immobilize biological moieties are described in U.S. Pat. No. 5,242,828. Poly-lysine is another option. An example of a use of poly-lysine layer on an 11-mercaptoundecanoic acid monolayer can be found in U.S. Pat. No. 5,629,213. The layer of affinity tag molecules can optionally instead constitute a phospholipid monolayer or a phospholipid bilayer, as described in PCT Publication WO 96/38726. Use of a phospholipid monolayer or bilayer as an affinity tag would be suitable if the biological moiety to be immobilized is a membrane protein, such as an ion channel protein.

Another major embodiment of devices of the present invention comprises an adaptor molecule that links the affinity tag to the immobilized biological moiety. The additional spacing of the biological moiety from the surface of the substrate (or coating) that is afforded by the use of an adaptor molecule is particularly advantageous if the biological moiety is a type of molecule which is known to be prone to surface inactivation, as is the case with proteins. One of ordinary skill in the art will be able to choose an adaptor molecule which is appropriate for a given affinity tag and/or biological moiety. For instance, if the affinity tag is streptavidin, then the adaptor molecule could be a biotin molecule that is chemically conjugated to the biological moiety. Alternatively, if the affinity tag is a phospholipid bilayer or monolayer then a membrane anchor could be chosen as a suitable adaptor molecule.

In one embodiment, the adaptor is a polypeptide, such as protein G or protein A. In a preferred embodiment, the affinity tag, adaptor molecule, and biological moiety together compose a fusion protein. Such a fusion protein may be readily expressed using standard recombinant DNA technology. Adaptor proteins are especially useful to increase the solubility of the protein of interest and to increase the distance between the surface of the substrate or coating and the protein of interest. Use of an adaptor protein or polypeptide can also be very useful in facilitating the preparative steps of protein purification by affinity binding. Examples of possible adaptor proteins include glutathione-S-transferase (GST), maltose-binding protein, chitin-binding protein, thioredoxin, green-fluorescent protein (GFP). GFP can also be used for quantification of surface binding.

Figure 8:
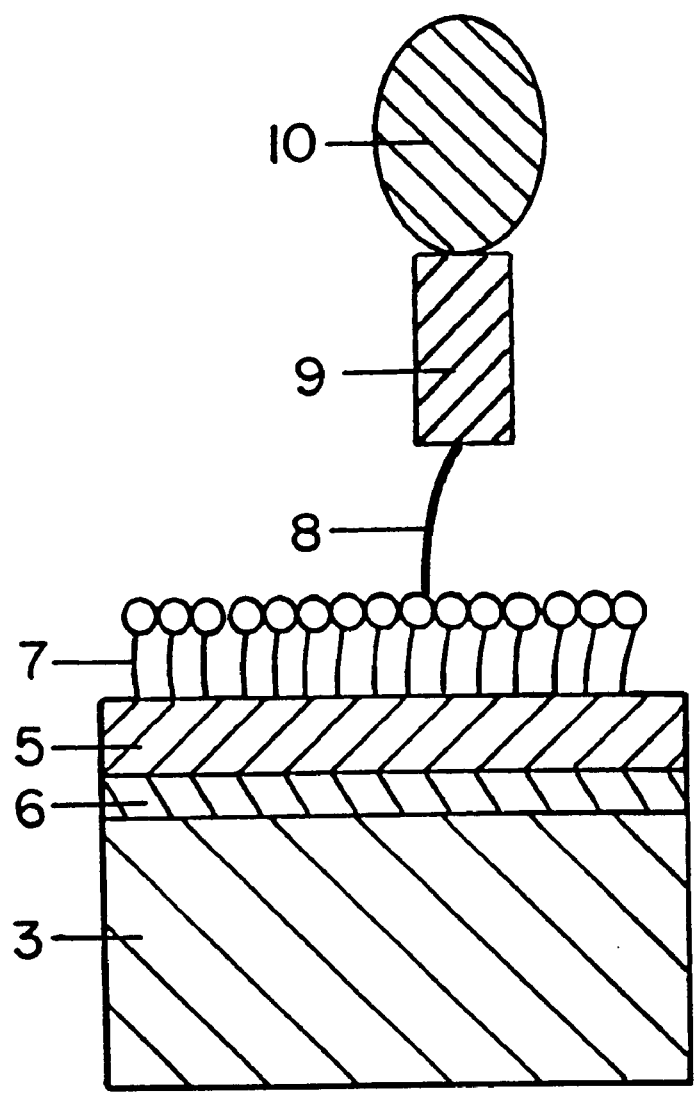
FIG. 8 shows a biological moiety immobilized on a monolayer-coated substrate via an affinity tag and an adaptor molecule.

FIG. 8 shows a biological moiety 10 immobilized on a monolayer 7 via both an affinity tag 8 and an adaptor molecule 9. The monolayer 7 has been formed on a coating 5 on a substrate 3. An interlayer 6 is also used between the coating 5 and the substrate 3.

In preparation for immobilization to the devices and arrays of the present invention, fusion proteins can be expressed from recombinant DNA either in vivo or in vitro. Amino acid affinity tags are introduced by polymerase chain reaction. Expression in vivo is in either bacteria (*Escherichia coli*), lower eukaryotes (*Saccharomyces cerevisiae, Saccharomyces pombe, Pichia pastoris*) or higher eukaryotes (bacculovirus-infected insect cells, insect cells, mammalian cells), or in vitro (*Escherichia coli* lysates, wheat germ extracts, reticulocyte lysates). Proteins are purified by affinity chromatography using commercially available resins.

DNA sequences encoding amino acid affinity tags and adaptor proteins are engineered into the expression vectors such that the genes of interest can be cloned in frame either 5' or 3' of the DNA sequence encoding the affinity tag and adaptor protein.

Figure 9:
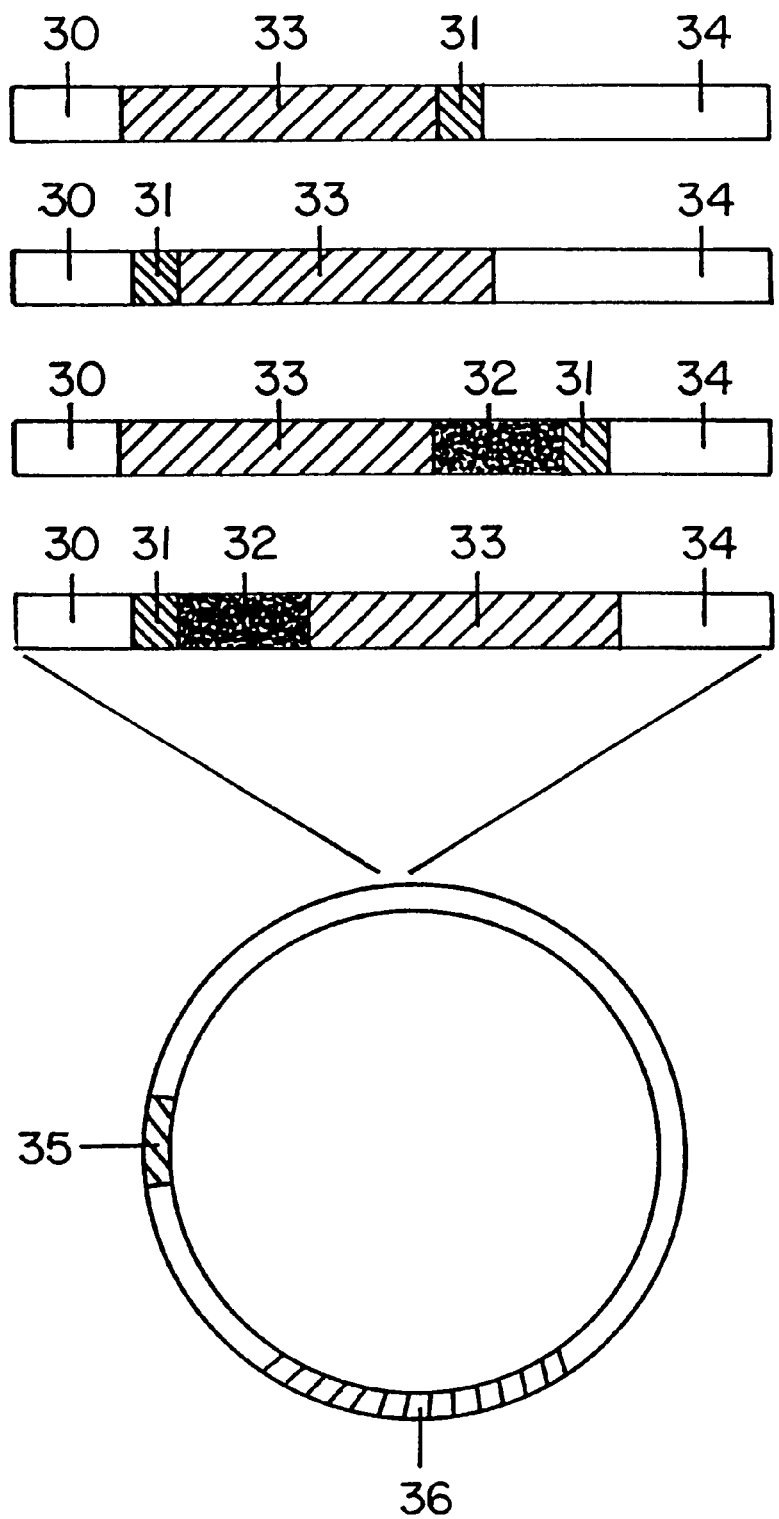
FIG. 9 shows four possible expression vectors for expressing fusion proteins of the desired protein and an affinity tag and, optionally, an adaptor molecule.

FIG. 9 shows four possible expression vectors useful for expressing a protein of interest, a polypeptide affinity tag, and a polypeptide adaptor molecule as a fusion protein. The vector contains an origin of replication sequence 35 and a gene 36 capable of conferring antibiotic resistance to a host cell. The insert of the vector contains a promoter sequence 30 and a termination signal sequence 34. Between the sequences 30 and 34, the insert also contains a gene 33 encoding the protein of interest and sequence 31, encoding the polypeptide affinity tag. Sequence 32 which codes for a polypeptide adaptor molecule may also be included in the plasmid construct and is positioned between the protein and affinity-tag coding regions (33 and 31, respectively).

Preferably, production of families of related proteins involves parallel processing from cloning to protein expression and protein purification. cDNAs for the protein of interest will be amplified by PCR using cDNA libraries or EST (expressed sequence tag) clones as templates. For in vivo expression of the proteins, cDNAs can be cloned into commercial expression vectors (Qiagen, Novagen, Clontech) and introduced into the appropriate organism for expression (organisms include: *Escherichia coli, Saccharomyces cerevisiae, Saccharomyces pombe, Pichia pastoris*, bacculovirus/insect cells, insect cells, mammalian cells). For in vitro expression PCR-amplified DNA sequences are directly used in coupled in vitro transcription, translation systems (*Escherichia coli* S30 lysates from T7 RNA polymerase expressing, preferably protease-deficient strains, wheat germ lysates, reticulocyte lysates with and without microsomes (Promega, Pharmacia, Panvera)). The choice of organism for optimal expression depends on the extent of post-translational modifications (i.e. glycosylation, lipid-modifications).

*Escherichia coli* based protein expression will be the method of choice for soluble proteins that do not require extensive post-translational modifications for activity. Extracellular or intracellular domains of membrane proteins will be fused to protein adaptors for expression and purification.

The entire approach can be performed using 96-well assay plates. PCR reactions are carried out under standard conditions. Oligonucleotide primers contain unique restriction sites for facile cloning into the expression vectors. Alternatively, the TA cloning system (Clontech) can be used. Expression vectors contain the sequences for affinity tags and the protein adaptors. PCR products are ligated into the expression vectors (under inducible promoters) and introduced into the appropriate competent *Escherichia coli* strain by calcium-dependent transformation (strains include: XL-1 blue, BL21, SG13009(lon-)). Transformed *Escherichia coli* cells are plated and individual colonies transferred into 96-array blocks. Cultures are grown to mid-log phase, induced for expression, and cells collected by centrifugation. Cells are resuspended containing lysozyme and the membranes broken by rapid freeze/thaw cycles, or by sonication. Cell debris is removed by centrifugation and the supernatants transferred to 96-tube arrays. The appropriate affinity matrix is added, protein of interest bound and nonspecifically bound proteins removed by repeated washing steps using 12–96 pin suction devices and centrifugation. Alternatively, magnetic affinity beads and filtration devices can be used (Qiagen). The proteins are eluted and transferred to a new 96-well array. Protein concentrations are determined and an aliquot of each protein is spotted onto a nitrocellulose filter and verified by Western analysis using an antibody directed against the affinity tag. The, purity of each sample is assessed by, SDS-PAGE and Coomassie staining or mass spectroscopy. Proteins are snap-frozen and stored at −80° C.

*Saccharomyces cerevisiae* allows for core glycosylation and lipid modifications of proteins. The approach described above for *Escherichia coli* can be used with slight modifications for transformation and cell lysis. Transformation of *Saccharomyces cerevisiae* is by lithium-acetate and cell lysis is either by lyticase digestion of the cell walls followed by freeze-thaw, sonication or glass-bead extraction. Variations of post-translational modifications can be obtained by different yeast strains (i.e. *Saccharomyces pombe, Pichia pastoris*).

The advantage of the bacculovirus system or mammalian cells are the wealth of post-translational modifications that can be obtained. The bacculovirus-system requires cloning of viruses, obtaining high titer stocks and infection of liquid insect cell suspensions (cells are SF9, SF21). Mammalian cell-based expression requires transfection and cloning of cell lines. Soluble proteins are collected from the medium while intracellular or membrane bound proteins require cell lysis (either detergent solubilization, freeze-thaw). Proteins can then be purified analogous to the procedure described for *Escherichia coli*.

For in vitro translation the system of choice is *Escherichia coli* lysates obtained from protease-deficient and T7 RNA polymerase overexpressing strains. *Escherichia coli* lysates provide efficient protein expression (30–56 µg/ml lysate). The entire process is carried out in 96-well arrays. Genes of interest are amplified by PCR using oligonucleotides that contain the gene-specific sequences containing a T7 RNA polymerase promotor and binding site and a sequence encoding the affinity tag. Alternatively, an adaptor protein can be fused to the gene of interest by PCR. Amplified DNAs can be directly transcribed and translated in the *Escherichia coli* lysates without prior cloning for fast analysis. The proteins are then isolated by binding to an affinity matrix and processed as described above.

Alternative systems which may be used include wheat germ extracts and reticulocyte extracts. In vitro, synthesis of membrane proteins and or post-translationally modified proteins will require reticulocyte lysates in combination with microsomes.

In one embodiment of the present invention, the biological moiety of one reactive site differs from the biological moiety of a second reactive site on the same device.

In another embodiment of the present invention, although the biological moiety of one reactive site is different from that of another, the two biological moieties are related. In a preferred embodiment the biological- moieties are members of the same protein family. The different biological moieties may be functionally related or just suspected of being functionally related. In another embodiment, however, the function of the biological moieties may not be entirely known. In these cases, the different biological moieties may either share a similarity in structure or sequence or be suspected of sharing a similarity in structure or sequence. In one embodiment, the different immobilized biological moieties may simply be fragments of different members of the same protein family. In another embodiment, the biological moieties may be known isozymes.

Examples of protein families preferred in the present invention include, but are not limited to, receptor families (examples: growth factor receptors, catecholamine receptors, amino acid derivative receptors, cytokine receptors, lectins), ligand families (examples: cytokines, serpins), enzyme families (examples: proteases, kinases, phosphatases, ras-like GTPases, hydrolases), and transcription factors (examples: steroid hormone receptors, heat-shock transcription factors, zinc-finger, leucine-zipper, homeodomain). In one embodiment, the different biological moieties are all HIV proteases. In another embodiment, the different biological moieties are all hepatitis C virus (HCV) proteases. Other examples of biological moieties of interest include antibodies and fragments thereof (such as Fab).

In an alternative embodiment of the invention device, the biological moieties of different reactive sites are identical to one another.

Although proteins, or fragments thereof, are the preferred biological moieties of the present invention, the immobilized biological moiety may optionally instead comprise a nucleic acid, a peptide-nucleic acid, a hormone, an antigen, an epitope, or any small organic molecule which either has or is suspected of having a physiological function.

Methods for using the devices of the present invention are provided by other aspects of the invention. The devices of the present invention are particularly well-suited for use in high-throughput drug screening. Other uses include medical diagnostics and biosensors. In each case a plurality of biological moieties or drug candidates or analytes can be screened in parallel. In one aspect of the invention, a method for screening a plurality of biological moieties in parallel for their ability to interact with a component of a fluid sample is provided. This method comprises delivering the fluid sample to the reactive sites of one of the invention devices having a different biological moiety immobilized on each reactive site and then detecting the interaction of said component with the immobilized biological moiety at each reactive site. The invention device is suitable for assaying both a catalytic reaction of an enzyme, a binding event, or a translocation by a membrane protein through a lipid bilayer.

Possible interactions towards which the present invention may be directed include, but are not limited to, antibody/antigen, antibody/hapten, enzyme/substrate, carrier protein/substrate, lectin/carbohydrate, receptor/hormone, receptor/effector, protein/DNA, protein/RNA, complementary strands of nucleic acid, repressor/inducer, or the like.

One embodiment of the present invention provides for a method of screening a plurality of biological moieties in parallel for their ability to react with a component of a fluid sample, comprising delivering the fluid sample to the reactive sites of a device of the present invention, wherein each reactive site of the device comprises a different biological moiety and detecting, either directly or indirectly, formation of product of the reaction of the component with the immobilized biological moiety at each reactive site.

Another embodiment of the invention provides a method for screening a plurality of biological moieties in parallel for their ability to bind a component of a fluid sample. This method comprises the following steps: delivering the fluid sample to the reactive sites of the invention device; washing the reactive site with fluid which does not contain the component in order to elute unbound component from the reactive sites; and detecting, either directly or indirectly, the presence, absence, or amount of the component retained at each reactive site.

An alternative method for screening a plurality of biological moieties for their ability to bind a component of a fluid sample comprises adding a known ligand of the biological moieties to the fluid sample, delivering the fluid sample to the reactive sites of the invention device, washing said reactive sites with fluid that does not contain either the known ligand or the component in order to elute unbound molecules of the known ligand and the component, detecting the presence of the known ligand retained at each reactive site, and, comparing retention of the known ligand detected with retention of the known ligand in the absence of the component.

A wide range of detection methods are applicable to this and other methods of the invention. The invention device can be interfaced with a means for detection of absorption in the visible range, chemiluminescence, or fluorescence (including lifetime, polarization, fluorescence correlation spectroscopy (FCS), and fluorescence-resonance energy transfer (FRET)). Furthermore, built-in detectors such as optical waveguides (PCT Publication WO 96/26432 and U.S. Pat. No. 5,677,196), surface plasmons, and surface charge sensors are compatible with many embodiments of the invention.

Figure 10:
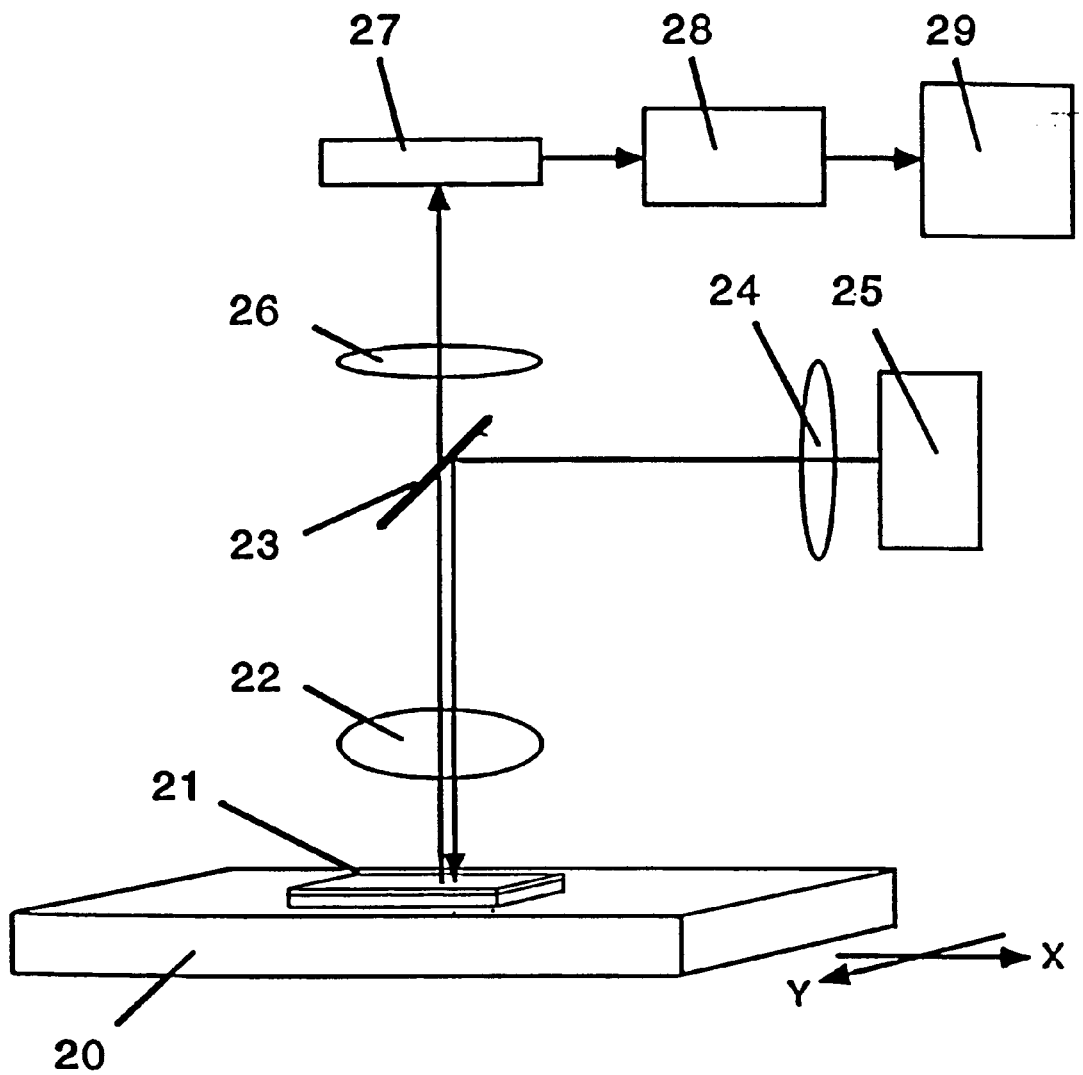
FIG. 10 shows a schematic diagram of a fluorescence detection unit which may be used to monitor interaction of the immobilized biological moieties of a microchannel array with an analyte.

FIG. 10 shows a schematic diagram of one type of fluorescence detection unit which may be used to monitor the interaction of immobilized biological moieties of a microchannel array with an analyte. In the illustrated detection unit, the microchannel array device 21 is positioned on a base plate 20. Light from a 100W mercury arc lamp 25 is directed through an excitation filter 24 and onto a beam splitter 23. The light is then directed through a lens 22, such as a Micro Nikkor 55 mm 1:2:8 lens, and onto the microchannels of the device 21. Fluorescence emission from the device returns through the lens 22 and the beam splitter 23. After also passing through an emission filter 26, the emission is received by a cooled CCD camera 27, such as the Slowscan TE/CCD-1024SF&SB (Princeton Instruments). The camera is operably connected to a CPU 28, which is, in turn, operably connected to a VCR/monitor 29.

To test the specificity of a drug candidate, its interaction with multiple members of a protein family is determined. Members of the protein family are separately immobilized in microchannels. The drug candidate's ability to interfere with protein activity, such as binding, catalytic conversion, or translocation of a ligand through a lipid bilayer, is then determined.

For instance, to test a drug candidate's ability to interfere with a protein binding event, the drug candidate and a known ligand of a member of the protein family that is labeled by a chemically-conjugated fluorescent moiety, are delivered in a fluid sample into each microchannel. After a short incubation period, the microchannels are flushed with fluid which lacks both the drug candidate and the ligand. The amount of fluorescent ligand remaining in each of the microchannels (and presumably bound to the protein molecules of that microchannel) can be detected by using a fluorescence detector/quantifier with optical access to the reactive site, either through a transparent or translucent cover or substrate.

To test a drug candidate's ability to interfere with a catalytic conversion of a ligand, drug candidate and ligand are delivered into the microchannel in a fluid sample and changes in the chromogenic or fluorescent properties can be detected by using an optical detector/quantifier with optical access to the reactive site, either through a transparent or translucent cover or substrate.

In a more general sense, the present invention provides for a method of screening the ability of a drug candidate to inhibit the reaction of a plurality of members of a protein family with their substrate, comprising the following steps: combining the drug candidate and the substrate in a fluid sample; delivering the fluid sample to the reactive sites of a device of the present invention, wherein each reactive site of the device comprises a different member of the protein family; and detecting, either directly or indirectly, for the inhibition of product formation at each reactive site.

To test a drug candidate's ability to interfere with the translocation of a ligand through a lipid bilayer, drug candidate and ligand are delivered in a fluid sample to each microchannel. After a short incubation period the microchannels may be flushed with fluid lacking ligand and the ligand accumulated between lipid bilayer and the device is determined by measuring changes in fluorescence, absorption, or electrical charge.

An alternative embodiment of the invention provides for a method for screening a plurality of drug candidates in parallel for their ability to inhibit a reaction of an enzyme with its substrate. This method first involves adding the enzyme's substrate to a plurality of fluid samples, each of which contains at least one of the drug candidates of interest. Next, each of the fluid samples is delivered to a reactive site of an invention device, such as the microchannel array. In this embodiment, each reactive site bears the immobilized enzyme. Finally, any inhibition of product formation at each reactive site (due to the presence of the drug candidate in the solution) is monitored.

Another aspect of the invention provides a method for screening a plurality of binding candidates in parallel for their ability to bind a biological moiety. This method comprises delivering different fluid samples, each containing at least one of the binding candidates, to the reactive sites of the invention device, washing the reactive sites with fluid which does not contain the binding candidate in order to elute unbound binding candidates, and detecting, either directly or indirectly, the presence of said binding candidate retained at each reactive site.

An alternative method for screening a plurality of binding candidates in parallel for their ability to bind a biological moiety is also provided by the present invention comprises the following: adding a known ligand of the biological moiety to a plurality of fluid samples, each of the fluid samples containing at least one of the binding candidates; delivering a different fluid sample to each of the reactive sites of the invention device, wherein multiple reactive sites comprise the same biological moiety; washing said reactive sites with fluid that contains neither the known ligand nor a binding candidate in order to elute unbound molecules of each; detecting the presence of the known ligand retained at each reactive site; and comparing retention of the known ligand detected with retention of the known ligand.in the absence of the binding candidate.

The present invention also provides for a method of pairing a plurality of proteins with their substrates. In this method, a fluid sample comprising a substrate of a known enzyme family is first delivered to the reactive sites of the invention device where each reactive site of the device comprises a different protein. Next, any suitable detection means may be used to detect, either directly or indirectly, for the presence of product formed by the reaction of the substrate with the protein of each reactive site.

In another aspect of the invention, a method for pairing a plurality of proteins with their ligands is provided. This method comprises delivering a fluid sample comprising a ligand of a known protein family to the reactive sites of the invention device; washing the reactive sites with fluid that does not contain the ligand to remove unbound ligand; and detecting, either directly or indirectly, the presence of the ligand retained at each reactive site.

The device of the present invention may also be used in a diagnostic manner. In the diagnostic embodiments of the invention, the different biological moieties of the reactive sites are not preferably members of the same protein family. One diagnostic use of the invention device is a method for detecting in a fluid sample the presence of a plurality of analytes which react with said biological moieties. The steps of this method comprise delivering the fluid sample to the reactive sites of the invention device; and detecting the interaction of the analyte with the immobilized biological moiety at each reactive site.

Another diagnostic method for detecting in a fluid sample the presence of a plurality of analytes which bind said biological moieties, comprises the following: delivering the fluid sample to the reactive sites of the invention device; washing said reactive sites with an analyte-free fluid to remove unbound analyte; and detecting, either directly or indirectly, the presence of analyte retained at each reactive site.

An alternative embodiment of the invention provides a device for processing a fluid sample that comprises a substrate, a plurality of parallel microchannels microfabricated into or onto said substrate; and a moiety immobilized within at least one of the parallel microchannels. In the device, the immobilized moiety is free to interact with a component of the fluid sample. In a preferred embodiment of this invention, the immobilized moiety is an immobilized biologicals moiety. In an especially preferred embodiment, the immobilized biological moiety is a protein.

The device may optionally comprise at least 10 parallel microchannels. In a preferred embodiment, the device comprises from about 100 to about 500 microchannels. In one embodiment, the device comprises from about 2 to about 500 parallel microchannels per $cm^2$.

The width of each of the microchannels is optionally between about 10 $\mu$m and about 500 $\mu$m. The depth of each of the microchannels is also optionally between about, 10 $\mu$m and about 500 $\mu$m.

One embodiment of the device further comprises a cover over at least a part of each of the microchannels. In one embodiment, the cover is a glass cover. The volume of each of the covered microchannels.may range from about 5 nanoliters to about 300 nanoliters. In a preferred embodiment, the volume of each of the covered microchannels is between about 10 nanoliters and about 50 nanoliters.

(c) Examples

The following specific examples are intended to illustrate the invention and should not be construed as limiting the scope of the claims:

Example 1

Fabrication of a Microchannel Array by Bulk Micromachining

In a preferred embodiment microchannel arrays are fabricated via standard microstereolithography into the device material (bulk micromachining). Alternative techniques include surface-micromachining and LIGA (injection molding). Usually, a computer-aided design pattern (reflecting the final channel geometries) is transferred to a photomask using standard techniques, which is then used to transfer the pattern onto a silicon wafer coated with photoresist.

In a typical example, the device ("chip"), with lateral dimensions of 50×15 mm, contains a series of 100 parallel channels separated with a spacing of 250 $\mu$m. Each channel is 5 mm long and has a cross-section of 100×100 $\mu$m. The channel volume is 50 nl. 4" diameter Si(100) wafers (Virginia Semiconductor) or 4" diameter Corning 7740 glass wafers are used as bulk materials. Si(100) wafers are first cleaned in a 5:1:1 DI water:$NH_3$:$H_2O_2$ bath (RCA1, 90° C., 10 min), followed by a 5:1:1 deionized (DI) water:HCl:$H_2O_2$ bath (RCA2, 90° C., 10 min) and finally passivated in 1% aqueous HF and singed at 150° C. for 30 min. After the wafer has been spincoated with polymethyl methacrylate PMMA as positive photoresist and prebaked for 25 minutes at 90° C., it is exposed using a Karl Suss contact printer and developed according to standard protocols. The wafer is then dried and postbaked at 110° C. for 25 min. Deep silicon reactive ion etching (RIE) is used to anisotropically dry-etch the channel features into the bulk material resulting in high aspect ratio, vertical sidewall features in the silicon (etch rate 2.5 $\mu$m/min). In the next step, the wafer is primed with a 20 nm thin titanium layer, followed by a 200 nm thin gold layer both layers deposited using electron-beam evaporation (5 Å/s, Thermionics). After resist stripping (acetone) and a short plasma treatment, the device is covered and sealed with a 50 $\mu$m thin glass cover (pyrex 7740) using low-temperature field assisted glass-silicon bonding resulting in a multichannel array with inlet and outlet ports. The gold-coated channel walls can then be further chemically modified to achieve the desired bioreactive and biocompatible properties (see Example 3, below).

Additional details of these procedures can be found in the following references: Madou, *Fundamentals of Microfabrication*, CRC Press (1997); Wolf and Tauber, *Silicon Processing for the VLSI Era, Vol. 1: Process Technology*, Lattice Press, (1986); and Thomson et al., *Introduction to Microlithography*, American Chemical Society, (1994).

Example 2

Fabrication of a Microchannel Array by Sacrificial Micromachining

In sacrificial micromachining, the bulk material is left essentially untouched. Various thick layers of other materials are built up by either physical vapor deposition (PVD), plasma-enhanced chemical vapor deposition (PECVD) or spin coating and selectively remain behind or are removed by subsequent processing steps. Thus, the resulting channel walls are chemically different from the bottom of the channels and the resist material remains as part of the microdevice. Typical resist materials for sacrificial micromachining are silicon nitride ($Si_3N_4$), polysilicon, thermally grown silicon oxide and organic resists such as epoxy-based SU-8 and polyimides allowing the formation of high aspect-ratio features with straight sidewalls.

In a typical example, the device ("chip"), with lateral dimensions of 50×15 mm, contains a series of 100 parallel-channels separated with a spacing of 250 $\mu$m. Each channel is 5 mm long and has a cross-section of 100×100 $\mu$m. The channel volume is 50 nl. 4" diameter Si(100) wafers (Virginia Semiconductor) or 4" diameter Corning 7740 glass wafers are used as bulk materials. Si(100) wafers are first cleaned in a 5:1:1 DI water:$NH_3$:$H_2O_2$ bath (RCA1, 90° C., 10 min), followed by a 5:1:1 deionized (DI) water:HCl:$H_2O_2$ bath (RCA2, 90° C., 10 min) and finally passivated in 1% aqueous HF and singed at 150° C. for 30 min. Spincoating of the wafer with EPON SU-8 results in a 100 $\mu$m thick film that is exposed similar to Example 1, above, and developed in a propyleneglycol-monomethyletheracetate (PGMEA) solution resulting in a multi-channel structure with high-aspect ratio vertical sidewalls. Deposition of metal films (20 nm Ti, 200 nm Au) is carried out as described in Example 1, above. The device is covered with a 50 $\mu$m thin adhesive glass cover. The gold-coated channel walls can then be further chemically modified to achieve the desired bioreactive and biocompatible properties (see Example 3, below).

Additional details on sacrificial micromachining processes can be found in Lorenz, et al., *Proceedings of MME'96 (Micro Mechanics Europe)*, Barcelona, Spain, October 1996, p. 32–35.

Example 3

Synthesis of an Aminoreactive Monolayer Molecule (Following the Procedure Outlined in Wagner et al., *Biophys. J.*, 1996, 70:2052–2066)

General. $^1$H- and $^{13}$C-NMR spectra are recorded on Bruker instruments (100 to 400 MHz). Chemical shifts ($\delta$) are reported in ppm relative to internal standard (($CH_3$)$_4$Si, $\delta$=0.00 ($^1$H- and $^{13}$C-NMR)). FAB-mass spectra are recorded on a VG-SABSEQ instrument ($Cs^+$, 20 keV). Transmission infrared spectra are obtained as dispersions in KBr on an FTIR Perkin-Elmer 1600 Series instrument. Thin-layer chromatography (TLC) is performed on pre-coated silica gel 60 F254 plates (MERCK, Darmstadt, FRG), and detection was done using $Cl_2$/toluidine, $PdCl_2$ and UV-detection under $NH_3$-vapor. Medium pressure liquid chromatography (MPLC) is performed on a Labomatic MD-80 (LABOMATIC INSTR. AG, Allschwil, Switzerland) using a Buechi column (460×3.6 mm; BUECHI, Flawil, Switzerland), filled with silica gel 60 (particle size 15–40 $\mu$m) from Merck.

Synthesis of 11,11'-dithiobis(succinimidylundecanoate) (DSU). Sodium thiosulfate (55.3 g, 350 mmol) is added to a suspension of 11-bromo-undecanoic acid (92.8 g, 350 mmol) in 50% aqueous 1,4-dioxane (1000 ml). The mixture is heated at, reflux (90° C.). for 2 h until the reaction to the intermediate Bunte salt was complete (clear solution). The oxidation to the corresponding disulfide is carried out in situ by adding iodine in portions until the solution retained with a yellow to brown colour. The surplus of iodine is retitrated with 15% sodium pyrosulfite in water. After removal of 1,4-dioxane by rotary evaporation the creamy suspension is filtered to yield product 11,11'-dithiobis(undecanoic acid). Recrystallization from ethyl acetate/THF provides a white solid (73.4 g, 96.5%): mp 94° C.; $^1$H NMR (400 MHz, $CDCl_3$/$CD_3OD$ 95:5): $\delta$ 2.69 (t, 2H, J=7.3 Hz), 2.29 (t, 2H, J=7.5 Hz), 1.76–1.57 (m, 4H), and 1.40–1.29 (m, 12H); FAB-MS ($Cs^+$, 20 keV): m/z (relative intensity) 434 (100, $M^+$). Anal. Calcd. for $C_{22}H_{42}O_4S_2$: C, 60.79; H, 9.74; S, 14.75. Found: C, 60.95; H, 9.82; S, 14.74. To a solution of 11,11'-dithiobis(undecanoic acid). (1.0 g, 2.3 mmol) in THF (50 ml) is added N-hydroxysuccinimide (0.575 g, 5 mmol) followed by DCC (1.03 g, 5 mmol) at 0° C. After the reaction mixture is allowed to warm to 23° C. and is stirred for 36 h at room temperature, the dicyclohexylurea (DCU) is filtered. Removal of the solvent under reduced pressure and recrystallization from acetone/hexane provides 11,11'-dithiobis(succinimidylundecanoate) as a white solid. Final purification is achieved by medium pressure liquid chromatography (9 bar) using silica gel and a 2:1 mixture of ethyl acetate and hexane. The organic phase is concentrated and dried in vacuum to afford 11,11'-dithiobis (succinimidylundecanoate) (1.12 g, 78%): mp 95° C.; $^1$H NMR (400 MHz, CDCl$_3$): δ 2.83 (s, 4H), 2.68 (t, 2H, J=7.3 Hz), 2.60 (t, 2H, J=7.5 Hz), 1.78–1.63 (m, 4H), and 1.43–1.29 (m, 12H); FAB-MS (Cs$^+$, 20 keV): m/z (relative intensity) 514 (100), 628 (86, M$^+$). Anal. Calcd. for $C_{30}H_{48}N_2O_8S_2$: C, 57.30; H, 7.69; N, 4.45; S, 10.20. Found: C, 57.32; H, 7.60; N, 4.39; S, 10.25.

Example 4

Formation of an Aminoreactive Monolayer on Gold (Following the Procedure of Wagner et al., Biophys. J., 1996, 70:2052–2066)

Monolayers based on 11,11-'dithiobis (succinimidylundecanoate) (DSU) are deposited on Au(111) surfaces of microdevices described under Examples 1 and 2 by immersing them into a 1 mM solution of DSU in chloroform at room temperature for 1 hour. After rinsing with 10 volumes of solvent, the N-hydroxysuccinimide-terminated monolayer are dried under a stream of nitrogen and immediately used for protein immobilization.

Example 5

Expression and Purification of HIV Protease Variants

The HIV protease (Genebank HIVHXB2CG) is an essential component of the HIV life cycle, and a major target in anti-viral therapy. HIV protease is required for the proteolytic processing of the gag and gag-pol gene products into functional proteins. Inhibition of HIV protease prevents the production of infectious viral progeny, and hence further rounds of infection. HIV protease belongs to the family of aspartic proteases and is a symmetric homodimer with an active site formed at the interface of the two 99 amino acids long subunits. The core residues in the active site consist of a conserved tripeptide motif (Asp-Thr-Gly) (Roberts et al., Science, 1990, 248:358). Resistant variants of HIV protease have emerged against all inhibitors currently used. Most prevalent mutations causing resistance individually or in combination are: L10R, D30N, M46I, L63P, A71V, V82F (Kaplan et al., Proc. Natl. Acad. Sci., 1994, 91:5597; Ho et al., J. Virol. 1994, 68: 2016; Condra et al., Nature, 1995, 374:569; Schock et al., J. Biol. Chem., 1996, 271:31957; Korant and Rizzo, Adv. Exp. Med. Biol., 1997, 421:279). Additional mutations that preserve protease activity are systematically generated (Loeb et al., Nature, 1989, 340:397).

Mutant proteases are generated by PCR mutagenesis (Weiner et al., Gene, 1994, 151:119) and expressed in Escherichia coli using two approaches: (i) mutant and wild-type protease cDNAs are cloned into a Escherichia coli expression vector containing a N-terminal histidine tag (H$_6$, SEQ ID NO:1; Hochuli et al., Biotechnology 1988, 6:1321) followed by a factor Xa cleavage site, while the stop codon of HIV protease is replaced by a sequence encoding a lysine tag (K$_6$, SEQ ID NO:2) followed by a stop codon. The resulting fusion protein is purified from inclusion bodies as described in Wondrak and Louis, Biochemistry, 1996, 35:2957, and the histidine tag removed by factor Xa as described in Wu et al., Biochemistry, 1998, 37:4518; or (ii) mutant and wild-type protease cDNAs are cloned into an Escherichia coli expression vector creating a fusion between HIV protease, a tri-glycine linker, glutathione S-transferase (GST) and a lysine-tag (HIV-GST-K$_6$). The autoprocessing site F*P at the carboxy terminus of the HIV protease is changed to F*I to prevent self-cleavage of the fusion proteins (Louis et al., Eur. J. Biochem., 1991, 199:361). The resulting proteins HIV-GST-K$_6$ are purified from Escherichia coli lysates by standard chromatography on glutathione agarose beads and stored in an amine-free buffer at –80° C. (25 mM HEPES, pH 7.5, 150 mM NaCl).

Example 6

Immobilization of Fusion Proteins on an Aminoreactive Monolayer

HIV protease variants, in the form of HIV-GST-K$_6$, and GST-K$_6$ are immobilized to the aminoreactive monolayer surface of the microchannel device (see Example 4, above). HIV-GST-K$_6$ and GST-K$_6$ are diluted to concentrations of 1 μg/ml in 25 mM HEPES buffer (pH 7.5) containing 150 mM NaCl. First, 50 μl of protein-free buffer is transferred through the channels to hydrate the monolayer surface. After 5 min of incubation, 10 μl of the corresponding protein solutions are flushed through the channels to guarantee total replacement with protein-containing solution. Immobilization is finished after 30 min at room temperature. The channels are rinsed with 50 μl immobilization buffer and subjected to analysis. Each microchannel displays a different HIV-GST-K$_6$ variant or control (GST-K$_6$). Ultrapure water with a resistance of 18 MΩcm is generally used for all aqueous buffers (purified by passage through a Barnstead Nanopure® system).

Example 7

Assay of Protease Activity in Microchannels

HIV protease requires at least a heptapeptide substrate (Moore et al., Biochem. Biophys. Res. Commun., 1989, 159:420). To analyze the activity of the different HIV variants, a continuous assay based on intra-molecular fluorescence resonance energy transfer (FRET) is used. A peptide substrate corresponding to the p17–p24 cleavage site of the viral gag protein (Skalka, Cell, 1989, 56:911) is modified by the addition of an energy-transfer pair (Geoghegan et al., FEBS Lett., 1990, 261:119): In Dns-Ser-Gln-Asn-Tyr-Pro-Ile-Val-Trp (Dns-SONYPIVW; SEQ ID NO:3), the Dns (dansyl) and Trp groups are the N- and C-terminal extensions, respectively. (Geoghegan et al.). Excitation of Trp is at 290 nm, and emission of Dns is at 575 nm. Cleavage of the peptide at the Tyr-Pro bond reduces the Dns emission and increases Trp emission at 360 nm. The modified heptapeptide Dns-SONYPIVW is prepared as described (Geoghegan et al.) and analyzed by amino acid analysis, nuclear magnetic resonance and mass spectrometry. The purity is checked by HPLC analysis using a Vydac C-4 column and an acetonitrile gradient in 0.1% TFA. In order to test the activity of all the HIV variants described above, each microchannel with an immobilized HIV variant (see Example 6) is filled with 20 μM of Dns-SQNYPIVW in 50 mM sodium acetate, pH 5.5, 13% glycerol, 10 mM DTT. Addition of the substrate to the immobilized proteins leads to time-dependent intensity changes in the fluorescence emission spectrum. The 360 nm Trp emission peak progressively will increase to about 2.5 times its initial intensity, while the Dns group's emission band (575 mm) will decline in intensity. This intensity change will be observed in all the channels containing active forms of the HIV variants. To control for changes in background fluorescence, GST-$K_6$ fusion protein is measured in parallel.

Competition assays can be carried, out to test the specificity of the proteolysis by the HIV variants. In one assay, both Dns-SQNYPIVW and a small organic molecule that is to be tested for its potential as a drug, is delivered in a 50 mM sodium acetate, pH 5.5, 13% glycerol, 10 mM DTT solution to each channel. An organic molecule which acts as an inhibitor for a wide range of HIV protease variants will diminish the Trp emission peak increase and the Dns emission band decrease associated with reaction of the protease with the peptide substrate in a number of the microchannels. A less desirable drug candidate, on the other hand, will inhibit the reaction of the HIV protease with the peptide substrate only in selected microchannels (or none at all).

Protease inhibitors Sequinavir (Roche), Ritonavir (Abbot) or Indinavir (Merck) can also be added to the reaction buffer and used as positive controls for the specificity of inhibition. Sequinavir will inhibit all the HIV variants except those containing either the G48V or the L90M mutation. Ritonavir in contrast is unable to block the activity of the M46I, L63P, A71V, V82F and the I84V variants. Indinavir has a similar inhibition pattern like Ritonavir except that the A71V variant is not affected. In addition Indinavir is not able to decrease the activity of the L10R HIV protease variant.

These experiments demonstrate how an HIV-variant microchannel device may be used to test the inhibitory effect of small organic molecules on the activity of the HIV protease.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A multi-channel sample detection device, comprising
   (a) a substrate having an upper surface,
   (b) a plurality of discrete open channels formed in or on said substrate adjacent said upper surface, each channel extending between first and second ends and having a bottom wall surface defining an immobilization region intermediate said first and second ends,
   (c) a cover attached to said substrate's upper surface and forming with each channel a closed channel having open first and second ends, said cover being part of a detection system for detecting interactions within each channel,
      where said first ends of said channels arranged so that said channels can each be both independently loaded with an analyte containing fluid, or simultaneously loaded with said fluid by loading said channels simultaneously with a bulk-loading dispenser device,
   (d) a plurality of immobilization molecules for immobilizing selected proteins or peptides or small molecules or nucleic acids, said immobilization molecules being chemisorbed or physisorbed to said immobilization region in each channel,
      wherein when said liquid containing said one or more analytes is introduced into said channels to interact with said peptides or proteins or small molecules or nucleic acids, such interactions, if any, can be detected by said detection device.

2. The device of claim 1, wherein at least one of said open ends is formed by said cover and said upper surface of said substrate.

3. The device of claim 1, wherein said channel have a cross-section that is between about 10 $\mu$m and 500 $\mu$m, and a length between about 1 to 20 mm.

4. The device of claim 1, wherein said cover is non-translucent or non-transparent.

5. The device of claim 1, wherein said cover is translucent or transparent.

6. The device of claim 1, wherein said reactive regions in said microchannels are oriented parallel to other reactive regions in other microchannels in said device.

7. The device of claim 1, wherein said immobilization molecules form an X-R-Y monolayer.

8. The device of claim 1, further comprising a metal coating disposed between said bottom wall surface within said immobilization regions and said immobilization molecules within such immobilization regions.

9. The device of claim 1, wherein said immobilization molecules form a lipid bilayer.

10. The device of claim 1, wherein said detector detects the product of a reaction.

* * * * *

UNITED STATES PATENT AND TRADEMARK OFFICE
CERTIFICATE OF CORRECTION

PATENT NO.   : 6,576,478 B1                                             Page 1 of 1
DATED        : June 10, 2003
INVENTOR(S)  : Peter Wagner et al.

It is certified that error appears in the above-identified patent and that said Letters Patent is hereby corrected as shown below:

Column 29,
Line 14, after "channels" insert -- are --.

Column 30,
Line 6, change "have" to -- has --.

Signed and Sealed this

Twenty-fifth Day of November, 2003

JAMES E. ROGAN
*Director of the United States Patent and Trademark Office*